(12) United States Patent
Cornay et al.

(10) Patent No.: US 7,189,196 B2
(45) Date of Patent: Mar. 13, 2007

(54) METHOD OF SEPARATING MATERIALS WITH A CONCENTRIC TUBULAR CENTRIFUGE

(75) Inventors: Paul J. Cornay, Longmont, CO (US); Ernest Peter Tovani, Englewood, CO (US); Gary Matzen, Longmont, CO (US)

(73) Assignee: ERTH Technologies, Inc., Longmont, CO (US)

( * ) Notice: Subject to any disclaimer, the term of this patent is extended or adjusted under 35 U.S.C. 154(b) by 433 days.

(21) Appl. No.: 10/723,366

(22) Filed: Nov. 26, 2003

(65) Prior Publication Data

US 2004/0142807 A1    Jul. 22, 2004

Related U.S. Application Data

(60) Division of application No. 09/828,296, filed on Apr. 6, 2001, now Pat. No. 6,966,874, and a continuation-in-part of application No. 09/707,430, filed on Nov. 6, 2000, now Pat. No. 6,808,481, which is a continuation of application No. 09/298,272, filed on Apr. 23, 1999, now Pat. No. 6,142,924, which is a continuation of application No. 08/950,377, filed on Oct. 14, 1997, now Pat. No. 5,944,648.

(60) Provisional application No. 60/215,499, filed on Jun. 30, 2000, provisional application No. 60/195,686, filed on Apr. 7, 2000.

(51) Int. Cl.
   B04B 5/02    (2006.01)
   B04B 11/00   (2006.01)

(52) U.S. Cl. ............................ 494/31; 494/37; 494/51; 494/84

(58) Field of Classification Search .................. 494/22, 494/31, 33, 37, 43–44, 50–54, 56, 76–78, 494/84–85; 210/294, 319, 360.1, 380.1, 210/380.3, 322; 29/428, 525.01
See application file for complete search history.

(56) References Cited

U.S. PATENT DOCUMENTS

| | | |
|---|---|---|
| 680,270 A | 8/1901 | Ohlsson |
| 717,385 A | 12/1902 | Gathmann |
| 778,355 A | 12/1904 | Freas |
| 785,910 A | 3/1905 | Nilsson |
| 949,226 A | 2/1910 | Goodman |
| 949,227 A | 2/1910 | Goodman |
| 1,097,561 A | 5/1914 | Resines |
| 1,124,907 A | 1/1915 | Jahn |
| 1,190,829 A | 7/1916 | Wendell |
| 1,239,734 A | 9/1917 | Sloan et al. |
| 1,510,657 A | 10/1924 | Coleman |
| 1,564,665 A | 12/1925 | Gates |
| 1,742,096 A | 12/1929 | Perrier |
| 1,783,546 A | 12/1930 | Petsche et al. |
| 1,854,313 A | 4/1932 | Petsche et al. |
| 2,185,279 A | 1/1940 | Strenzynski |
| 2,450,737 A | 10/1948 | Rundquist |
| 3,150,944 A | 9/1964 | Nerad |
| 3,623,656 A | 11/1971 | Lavanchy |
| 3,685,721 A | 8/1972 | Kohama |
| 3,837,491 A | 9/1974 | Huminston et al. |
| 4,073,431 A | 2/1978 | Jager |
| 4,108,763 A | 8/1978 | Clough |
| 4,369,115 A | 1/1983 | Bauer |
| 4,500,324 A | 2/1985 | Vuong |
| 4,617,010 A | 10/1986 | Epper et al. |
| 4,618,478 A | 10/1986 | McKinney |
| 4,648,863 A | 3/1987 | Nees |
| 4,673,510 A | 6/1987 | Janusch et al. |
| 4,911,738 A | 3/1990 | Schneider |
| 5,045,202 A | 9/1991 | Stearns et al. |
| 5,132,025 A | 7/1992 | Hays |
| 5,156,751 A | 10/1992 | Miller |
| 5,240,619 A | 8/1993 | Copa et al. |
| 5,252,224 A | 10/1993 | Modell et al. |
| 5,372,725 A | 12/1994 | Halff et al. |
| 5,380,442 A | 1/1995 | Yan |
| 5,425,883 A | 6/1995 | Reid et al. |
| 5,462,676 A | 10/1995 | Pitts |

| | | | |
|---|---|---|---|
| 5,470,481 A | 11/1995 | Modell et al. | |
| 5,500,120 A | 3/1996 | Baker | |
| 5,538,636 A | 7/1996 | Gnann et al. | |
| 5,620,606 A | 4/1997 | McBrayer, Jr. et al. | |
| 5,651,897 A | 7/1997 | Lehmann | |
| 5,688,377 A | 11/1997 | McCutchen | |
| 5,688,399 A | 11/1997 | Halff et al. | |
| 5,792,351 A | 8/1998 | Wehrle et al. | |
| 5,888,389 A | 3/1999 | Griffith et al. | |
| 5,928,522 A | 7/1999 | Conaway | |
| 5,944,648 A | 8/1999 | Cornay | |
| 5,997,812 A | 12/1999 | Burnham et al. | |
| 6,051,145 A | 4/2000 | Griffith et al. | |
| 6,080,309 A | 6/2000 | Reid et al. | |
| 6,093,328 A | 7/2000 | Santina | |
| 6,142,924 A | 11/2000 | Cornay | |
| 6,217,502 B1 | 4/2001 | Hallgren et al. | |
| 6,251,290 B1 | 6/2001 | Conaway | |
| 6,309,338 B1 | 10/2001 | Christensen | |
| 6,508,752 B1 | 1/2003 | Hallgren et al. | |
| 6,808,481 B1 | 10/2004 | Cornay | |
| 6,966,874 B2 * | 11/2005 | Cornay et al. | 494/33 |
| 2002/0032111 A1 * | 3/2002 | Cornay et al. | 494/37 |
| 2004/0142807 A1 * | 7/2004 | Cornay et al. | 494/51 |
| 2005/0054507 A1 * | 3/2005 | Cornay et al. | 494/33 |
| 2005/0178733 A1 * | 8/2005 | Conger et al. | 210/760 |

FOREIGN PATENT DOCUMENTS

| | | |
|---|---|---|
| EP | 0545683 | 7/1996 |
| EP | 0928227 | 1/2003 |
| GB | 18147 | 9/1907 |
| GB | 269193 | 4/1927 |
| GB | 1526129 | 9/1978 |
| JP | 57004299 | 1/1982 |
| JP | 58034098 | 2/1983 |
| JP | 58095589 | 6/1983 |
| JP | 58205591 | 11/1983 |
| JP | 62007489 | 1/1987 |
| JP | 03293097 | 12/1991 |
| JP | 05068980 | 3/1993 |
| SE | 189162 | 4/1964 |
| WO | WO99/025497 | 5/1999 |
| WO | WO01005498 | 1/2001 |

OTHER PUBLICATIONS

CARR Separations, Inc.; CARR Powerfuge® Separation System, P6 Brochure; at least Jan. 14, 1997.
CARR Separations, Inc.; CARR Powerfuge® Separation System, P12 Brochure; at least Jan. 14, 1997.
CARR Separations, Inc.; CARR Powerfuge® Separation System, P18 Brochure; at least Jan. 14, 1997.
CARR Separations, Inc.; CARR Powerfuge® Separation System, P24 Brochure; at least Jan. 14, 1997.
CARR Separations, Inc.; CARR Powerfuge® Separation System, Pilot for Hazardous Areas Brochure; at least Jan. 14, 1997.
CARR Separations, Inc.; CARR Powerfuge® Separation System Pilot Dimensions; at least Jan. 14, 1997.
CARR Separations, Inc.; CARR Powerfuge™ Brochure "Breakthrough Centrifuge Technology"; at least Jan. 14, 1997.
CARR Separations, Inc.; Chemical Processing Brochure; Jan. 1998.
CARR Separations, Inc.; Sub-micron Classification and Recovery Brochure; at least Jan. 14, 1997.
Sharples™ Maximizer™ XM; available as early as Jun. 1997.
Alfa-Laval Centrifuges for the Chemical Process Industries.
Alfa-Laval Waste Oil Recovery.
Oiltools Solids Control Equipment.
Alfa-Laval ALFAX Self-Cleaning Centrifuge Separators.
TRW Brandt Decanting Centrifuges.
Alfa-Lava "When to use a disk-stack centrifuge".
Michem's New RMS™ Model 3SMD Centrifuge.
Alfa-Laval "Slop Oil Treatment Plant for Crude Oil Recovery".
Geosource Geolograph Pioneer Manual of Centrifuge Operation.
Investor Brochure, Paul J. Cornay, "G-Force corp.", 1988.
Author Unknown, "Jet mixers for agitating large storage tanks," Chem. Eng (Int. Ed.), vol. 96, No. 1, p. 133, Jan. 16, 1989.
Butcher, C., "Liquid waste solutions," Chemical Engineer (Rugby-UK), No. 551, pp. s27, Oct. 14, 1993.
Min et al., "Advanced treatment of piggery wastewater by MAP, precipitation, and ozone oxidation process using pilot plant," Journal of Korea Solid Wastes Engineering Society, vol. 15, No. 6, pp. 644-652, Sep. 1998.
Sereno et al., "Dewatered sludge storage emissions control using multistage wet scrubbing," Water Environment Research, vol. 65, No. 1, pp. 66-72, 1993.
Theriault et al., "The effect of chemical, physical and enzymatic treatments on the dewatering of tar sands tailings," Fuel, vol. 74, No. 9, pp. 1404-1412, Sep. 1995.

* cited by examiner

*Primary Examiner*—Charles E. Cooley
(74) *Attorney, Agent, or Firm*—Dorsey & Whitney LLP

(57) ABSTRACT

A two-tube centrifuge separates light material and heavy material from an input mixture. A hollow drive shaft rotates a central body member about an axis of rotation. Two hollow arm assemblies, each having circular cross-section, are mounted on diametrically opposite sides of the central body. Each arm assembly includes an outer housing tube, an intermediate tube, and an inner tube that is longer than the intermediate tube. An end cap having a removable plug is mounted on the outer end of the housing-tube of each arm assembly. The inner ends of all three tubes are mechanically interlocked in a manner to cantilever mount the inner and intermediate tubes to the central-body with their outer ends spaced from the internal surface of the end cap. An input-mixture path extends through the hollow drive shaft, through the central-body, and into a cylindrical space between the inner and intermediate tubes of each arm assembly. A heavy material exit path extends from the inner tube, through the central body, and into an exit cone that lies diametrically opposite the drive shaft and whose axis is coincident with the axis of rotation. A light material exit path extends from a cylindrical space between the inner and intermediate tubes, through the central-body, and through a wall of the exit cone. The inner tube of each arm assembly includes an auger. An electric motor drives the drive shaft. A hydraulic motor drives the auger. An oxidation reactor in a centrifuge for decanting lighter material from heavier material from a mixture of initial material and to perform an oxidation reaction process on the heavier material.

6 Claims, 24 Drawing Sheets

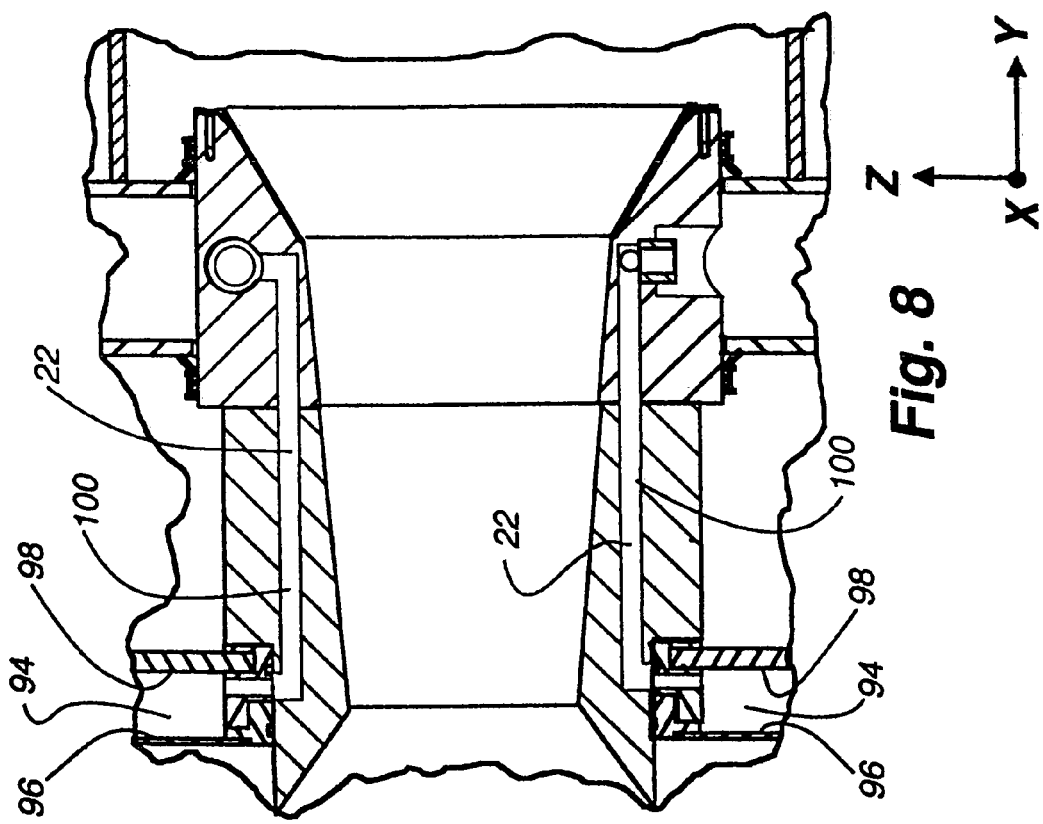
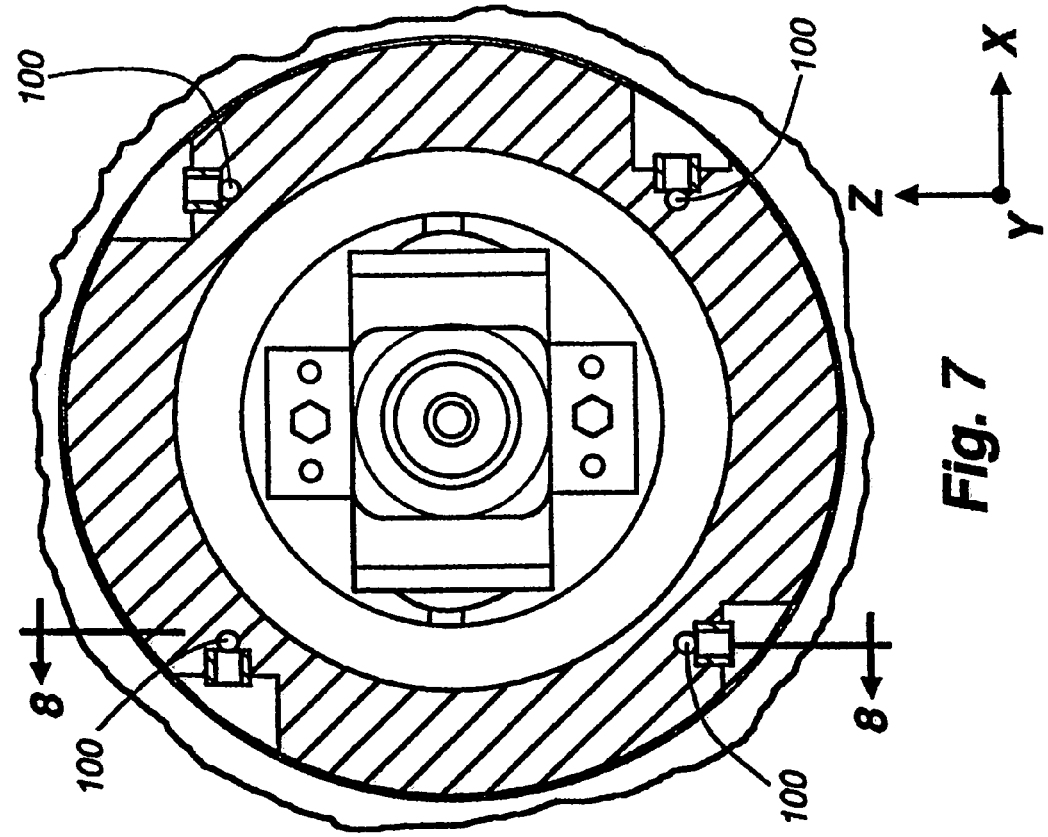

METHOD OF SEPARATING MATERIALS WITH A CONCENTRIC TUBULAR CENTRIFUGE

CROSS-REFERENCE TO RELATED APPLICATIONS AND U.S. PATENTS

This application is a divisional patent application of U.S. patent application Ser. No. 09/828,296, filed Apr. 6, 2001, entitled CONCENTRIC TUBULAR CENTRIFUGE, now U.S. Pat. No. 6,966,874; which claims the benefit of U.S. Provisional Application Ser. No. 60,215,499, filed Jun. 30, 2000, entitled CONCENTRIC TUBULAR CENTRIFUGE and U.S. Provisional Application Ser. No. 60/195,686, filed Apr. 7, 2000, entitled CENTRIFUGAL OXIDATION REACTOR and is a continuation-in-part of U.S. patent application Ser. No. 09/707,430 filed Nov. 6, 2000, entitled CONCENTRIC TUBULAR CENTRIFUGE, now U.S. Pat. No. 6,808,481; which is a continuation of U.S. patent application Ser. No. 09/298,272 filed Apr. 23, 1999, entitled CONCENTRIC TUBULAR CENTRIFUGE, now U.S. Pat. No. 6,142,924; which is in turn a continuation application of U.S. patent application Ser. No. 08/950,377 filed Oct. 14, 1997, entitled CONCENTRIC TUBULAR CENTRIFUGE, now U.S. Pat. No. 5,944,648, which claims the benefit of U.S. Provisional Patent Application Serial No. 60/028,556, filed Oct. 15, 1996, entitled CONCENTRIC TUBULAR CENTRIFUGE; all of which are incorporated herein by reference as if fully set forth herein.

FIELD OF THE INVENTION

This invention relates to centrifuges and more particularly to centrifuges used as oxidation reactors.

BACKGROUND OF THE INVENTION

Centrifuge technology has long been used to separate mixtures of materials into their heavy and light components. Centrifuge technology is useful in many fields, including, but not limited to, medical, industrial, and public service sectors, all within various specific applications where separation technology is beneficial.

The effectiveness of presently known centrifuge technology is dependent upon factors such as the magnitude of the separating force (centrifugal force) that is generated by the centrifuge and the residence time during which the material to be separated is subjected to the separating force. Virtually all centrifuges rely on some type of rotary motion to generate a separating force. Thus, the magnitude of the separating force that is generated depends on the size (moment arm) of the centrifuge and the speed at which the centrifuge rotates. To generate a given magnitude of separating force, a small-size centrifuge must be driven at higher revolutions per minute (RPM) than is required of a large-size centrifuge.

The residence time during which the material to be separated is subjected to the separating force depends upon the flow-path of the material through the centrifuge. This flow-path is defined by the internal structure of the centrifuge, and its length is sometimes limited by the type of centrifuge. Typically, the longer the residence time of a material under a given separation force, the better the separation of the light material from heavy material.

Existing centrifuge technology is limited in its ability to allow a change to be made in the separation force and/or in the residence time.

While existing relatively large-size centrifuge technology is capable of handling relatively large inflow rates, such as 100 gallons per minute (GPM), it is not conducive to portable use in a self-contained unit. Such large size centrifuge structures are difficult to transport, require frequent skilled maintenance, and often do not allow simple modification of the separation force and/or the residence time in order to adjust the centrifuge as input material conditions or output material requirements vary.

In present supercritical oxidation reactors, a complex mechanical system is required for creating the environment necessary to perform the supercritical oxidation reaction. For instance, in these complex systems significant effort is given to controlling the pressure, both increasing the pressure to that required for the process and then decreasing the pressure to allow waste removal. The associated equipment can be expensive to build and possibly dangerous to operate. The supercritical reaction systems presently available typically incorporate several steps in order to sequentially build up the required pressure and temperature to adequately perform the supercritical reaction process. These systems are expensive and have relatively low throughput.

What is needed in the art is an apparatus to allow the performing of the oxidation reaction, both supercritical and subcritical, which is inexpensive, relatively simple to operate, allows continuous processing of relatively high flow rates, and is easy to maintain and repair.

It is with the foregoing issues in mind that the centrifuge of the present invention was developed.

SUMMARY OF THE INVENTION

This invention provides a centrifuge having at least one arm assembly that rotates in a generally vertical plane and that extends outward on a common radius from a generally horizontal axis of rotation (spin axis).

The present invention pertains to a centrifuge for accepting an input mixture and for separating a light material that is within the mixture from a heavy material that is within the mixture. The centrifuge has a housing having a central member that is rotatable on an axis of rotation and also has at least one arm assembly used for separation of the light material from the heavy material. The housing is constructed such that the lower half of the housing can be placed below ground level. The arm assembly has an outer tube with a first end operably connected to the central member and a closed second end extending away from the central member. The arm assembly has an intermediate tube operably connected to the central member that is located within the outer housing. This location defines a first annular flow path between the outer housing and the intermediate tube. The arm assembly also has an inner tube that is operably connected to the central member that is located within the intermediate tube. This location with respect to the intermediate tube defines a second annular flow path between the intermediate tube and the inner tube as well as a tubular flow path within the inner tube. An input mixture flow path is provided to receive the input mixture. This input mixture flow path extends through the drive shaft, through the housing and is in communication with one of the first and second annular flow paths. There is also a light material flow path communicating with the other of the first and second annular flow paths and a heavy material flow path communicating with the tubular flow path.

According to another aspect of the present invention, the outer tube housing is operably connected to the central member by a first mounting ring. The intermediate tube is operably connected to the central member and the first mounting ring by a second mounting ring and the inner tube is operably connected to the central member and the second mounting ring by a third mounting ring. The first mounting ring has an overhanging portion that overlies a portion of the second mounting ring, the second mounting ring has an overhanging portion that overlies a portion of the third mounting ring.

A first speed-controllable drive means drives a hollow drive shaft that defines the centrifuge's horizontal axis of rotation. One end of this drive shaft is bolt connected to a central member that rotates on the axis of rotation. The arm assembly is mounted onto this central member and is contained within a relatively large annular housing that is formed generally concentric with the axis of rotation. The centrifuge's separation force is a direct function of the speed of this first drive means and this force is varied by varying the speed of the motor. The residence time of the centrifuge is related to the length of the arms and the number of cylindrical tubes, which can be changed as desired.

The inner tube of each centrifuge arm assembly is a long tube having a small diameter. This inner tube may contain an elongated conveyer screw or auger that aids in the transport of heavy material radially inward toward the axis of rotation. A flow of heavy material enters the far end of this inner tube, moves inward toward the central member, enters the central member and makes a 90° degree turn in a direction away from the drive shaft, flows into the apex of a heavy-material discharge cone, through the discharge cone, and then into a small-size annular housing that is formed concentric with the axis of rotation.

This heavy material discharge cone extends outward from the central member. The horizontal axis of the discharge cone is generally coincident with the centrifuge's axis of rotation, and the discharge cone is located on the opposite side of the central member from the drive shaft.

A second speed-controllable drive means is mounted onto the central member, generally coincident with the centrifuge's axis of rotation. This second drive means is connected to drive the conveyor screw. Speed-control of this second drive means enables the speed of conveyor screws to be controlled independent of the speed at which the centrifuge's arm assemblies are rotated by the first drive means.

The intermediate tube of the centrifuge arm assembly is of an intermediate length and an intermediate diameter. An input mixture that is to be separated, and that contains both heavy and light material, flows through the hollow drive shaft and into the central member where it makes a 90° turn, flows into the inner end of an annular space that exists between the inner tube and the intermediate tube, and then flows outward from the axis of rotation to the outer end of the arm assembly.

The outer housing of each centrifuge arm assembly has the shortest length and the largest diameter. Light material that has been separated from the input mixture flows into the outer end of a cylindrical space that exists between the intermediate tube and the outer housing, inward toward the axis of rotation, into the central member where it makes a 90° degree turn, through conduits that are formed in a side wall of the heavy material discharge cone, and then into an intermediate size annular housing that is formed concentric with the axis of rotation.

As a feature of the invention, the two centrifuge arm assemblies provide for selective replacement of components that are within the arm assembly(s), and provide for modification of the arm assemblies in order to change the separation characteristics of the centrifuge. This is achieved by including a removable plug and/or a removable end cap on the end of the outer tube housing.

According to another aspect of the present invention, a method of using a centrifuge to separate a light material that is within an input mixture from a heavy material that is within the input mixture, while at the same time independently controlling a speed of rotation of the centrifuge and a speed of removal of the heavy material from the centrifuge is provided. The method includes the following steps: providing a first and a second arm assembly aligned on an arm-axis and that are rotatable in a plane extending generally perpendicular to a rotation-axis; providing that each of the arm assemblies includes a tubular-housing having a closed outer end, an intermediate tube having an open outer end, and an inner tube having an open outer end; providing that the inner tube of each arm assembly is of a given length; providing that the intermediate tube of each arm assembly is of a length that is less than the given length; providing that an outer end of the tubular-housing of each arm assembly is spaced from the outer end of the intermediate tube and from the outer end of the inner tube; providing an input mixture flow path that communicates with a cylindrical space between the intermediate tube and the inner tube of each arm assembly; providing a heavy material flow path that communicates with a space within the inner tube of each arm assembly; providing a light material flow path that communicates with a cylindrical space between the intermediate tube and the tubular-housing of each arm assembly; providing a conveyer screw within the inner tube of each arm assembly; providing a first speed controllable drive means connected to effect rotation of the first and second arm assemblies about the rotation-axis; and providing a second speed controllable drive means connected to effect rotation of the conveyer screws.

In an embodiment of the invention, but without limitation thereto, the input mixture to the centrifuge of the invention is a water-containing liquid that is not potable, and the light material output from the centrifuge comprises potable water.

The present invention includes a novel system and method for oxidizing materials. In both the system and method embodiments, an oxidation reaction is contained within a centrifuge.

The system for oxidizing materials includes an entry zone, a thickening zone, a reaction zone, a cooling zone, and an exit zone. The entry zone includes a centrifuge influent manifold and beginning portion of a centrifuge arm, the reaction zone encompasses the end portion of a centrifuge arm, the cooling zone is contained in the center channel of a centrifuge arm, and the exit zone includes the centrifuge effluent manifold. Influent materials are introduced to the system via the entry zone. The influent materials are then thickened in the thickening zone before being transported to the reaction zone. In the reaction zone, the materials are oxidized in an oxidation reaction. The oxidation by-products (effluent) are next cooled in the cooling zone before exiting the system via the exit zone.

The method for oxidizing materials involves passing an influent material through the various system zones (entry zone, thickening zone, reaction zone, cooling zone, and exit zone) described above. In addition to oxidizing the influent materials, lighter fluids present in the influent materials may be decanted during the normal operation of the centrifuge if desired. By controlling the system probe, the volume of centrate produced can be controlled.

The centrifuge can be used as a supercritical oxidation reactor or a subcritical oxidation reactor, depending on the conditions inside the reactor, as controlled by the user. Given the extreme pressure built up in the end of each arm of the centrifuge as described herein, the end of each arm can act as the reaction zone for the supercritical oxidation reactor with the proper addition of an oxidant into the system and with the proper addition of heat to create the ideal reaction zone parameters.

The instant centrifuge can be used as an oxidation reactor, both for subcritical and supercritical conditions. In this embodiment, the centrifuge includes a main body having at least one inlet and at least one outlet and being rotatable about an axis, at least one hollow arm extending from said main body, said arm having a distal end and a proximal end, said arm defining at least an interior inlet flow path communicating with and leading from said inlet at said proximal end outwardly to said distal end, and at least a first exit flow path leading from said distal end to said proximal end and communicating with said outlet, and a heat source at said distal end, and a reactor region formed at said distal end of said arm.

In greater detail, the oxidation reactor could also include a flow path for inserting an oxidant into to said reactor region.

In further detail, the oxidation reactor could also include a second exit flow path leading to a second outlet, said first exit flow path for the flow of the incoming material after passing through said reactor region, and said second exit flow path for liquid separated from the incoming material.

In further embodiments, the oxidation reactor can be suspended from a frame so as to rotate about a vertical axis, and the outlet of the oxidation reactor can be positioned in a tank below the frame. The tank can have liquid, such as water, therein to assist in handling the reaction by-products.

Other aspects, features and details of the present invention can be more completely understood by reference to the following detailed description of a preferred embodiment, in conjunction with the drawings, and from the attached claims.

BRIEF DESCRIPTION OF THE DRAWINGS

In the figures of this application an X-Y-Z coordinate system is shown as an aid to orienting the figures one to another.

FIG. 7 is a section view taken on the line 6—6 of FIG. 5, this view showing four light-product flow paths that supply the light-product output to the intermediate-size annular housing shown in FIG. 1.

FIG. 8 is a section view taken along the line 7—7 of FIG. 7, this view showing a cross section of the centrifuge's heavy-product output cone, and this figure also showing two of the four light-product flow paths of FIG. 7 in greater detail.

DETAILED DESCRIPTION OF PREFERRED EMBODIMENTS

Figure 1:
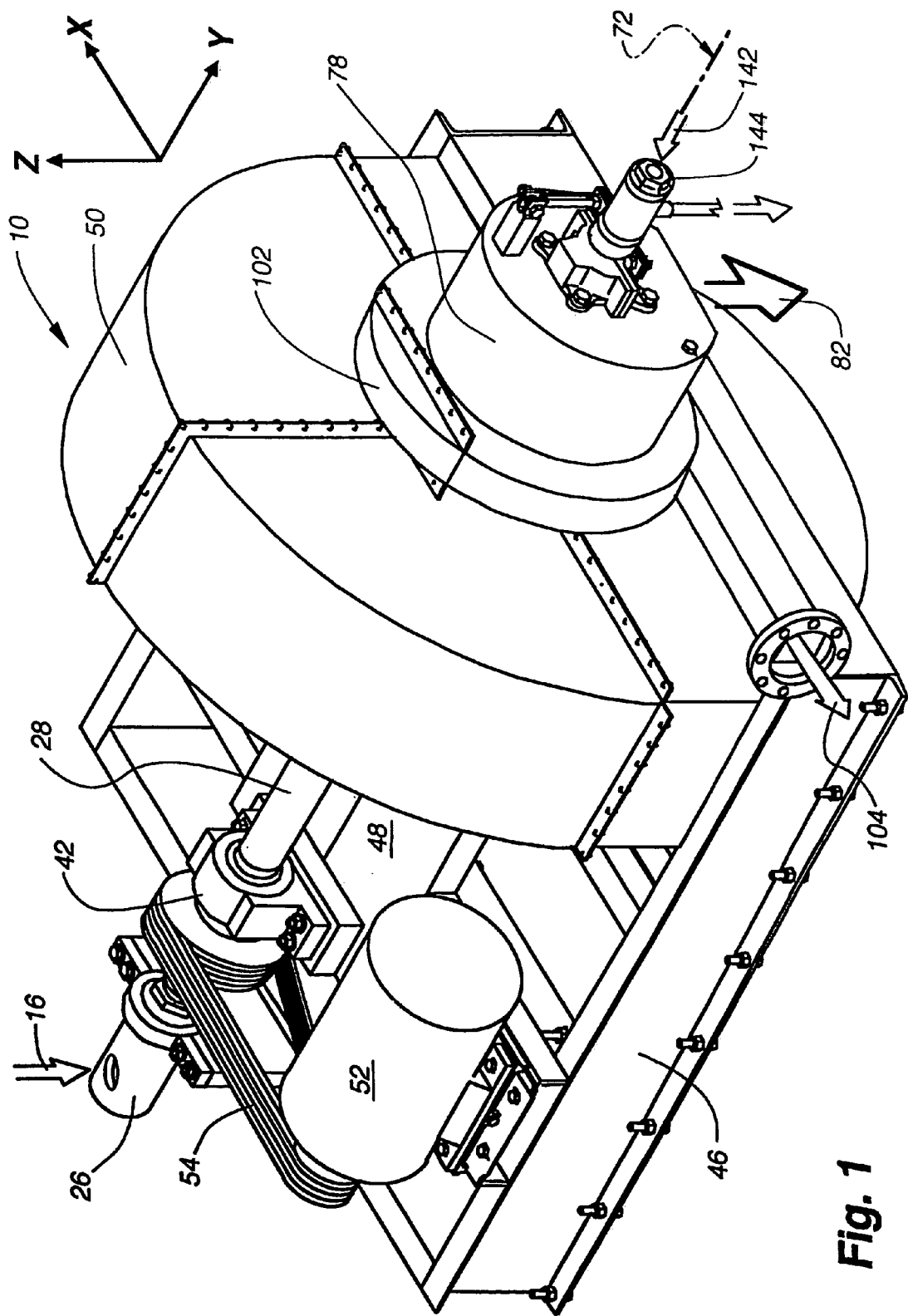
FIG. 1 is a top and right side perspective view of a centrifuge in accordance with the present invention wherein an input mixture to be separated enters the centrifuge by way of a hollow drive shaft that supports a rotating arm assembly within a large-size and vertical-standing annular housing, this view showing a rectangular frame and frame-mounted electric motor and belt that drive the drive shaft, this view showing an intermediate-size annular housing out of which light material flows, and this view showing a small-size annular housing out of which heavy material flows.

This invention will be described relative to the separation of an input mixture that contains heavy solids and relatively light liquids. However, the invention can be used with virtually any generally liquid input mixture that contains both heavy and light material, for example a mixture of oil and water. Also, the input mixture can be filtered prior to being introduced into the centrifuge of the invention.

The input mixture can be introduced into the centrifuge by way of gravity feed or by way of pressure feed as achieved by pumping. The centrifuge 10 of the present invention is relatively insensitive to the flow-rate of its input mixture, to the solid content of its input mixture, and to the volumetric weight of its input mixture.

FIGS. 1–12 show a centrifuge 10 in accordance with this invention. Important features of this invention include, but are not limited to, a rotating assembly 12, 14 that rotates in a X-Z vertical plane; independent motor-drive of rotating assembly 12, 14 and horizontally extending conveyer screws or augers 36 that aid in the transport of heavy material out of centrifuge 10; an end-cap/multiple-bold/interlocking-base construction and arrangement by which two concentric tubes 30, 32 and an outer concentric tube-housing 34 defining the flow path of the material that can be easily disassembled/reassembled in order to repair/modify the centrifuge's rotating assembly 12, 14; a wide, cone-shaped, exit path 18 by which the heavy material exits centrifuge 10; and the exit path(s) 20 of the lighter material.

Figure 4:
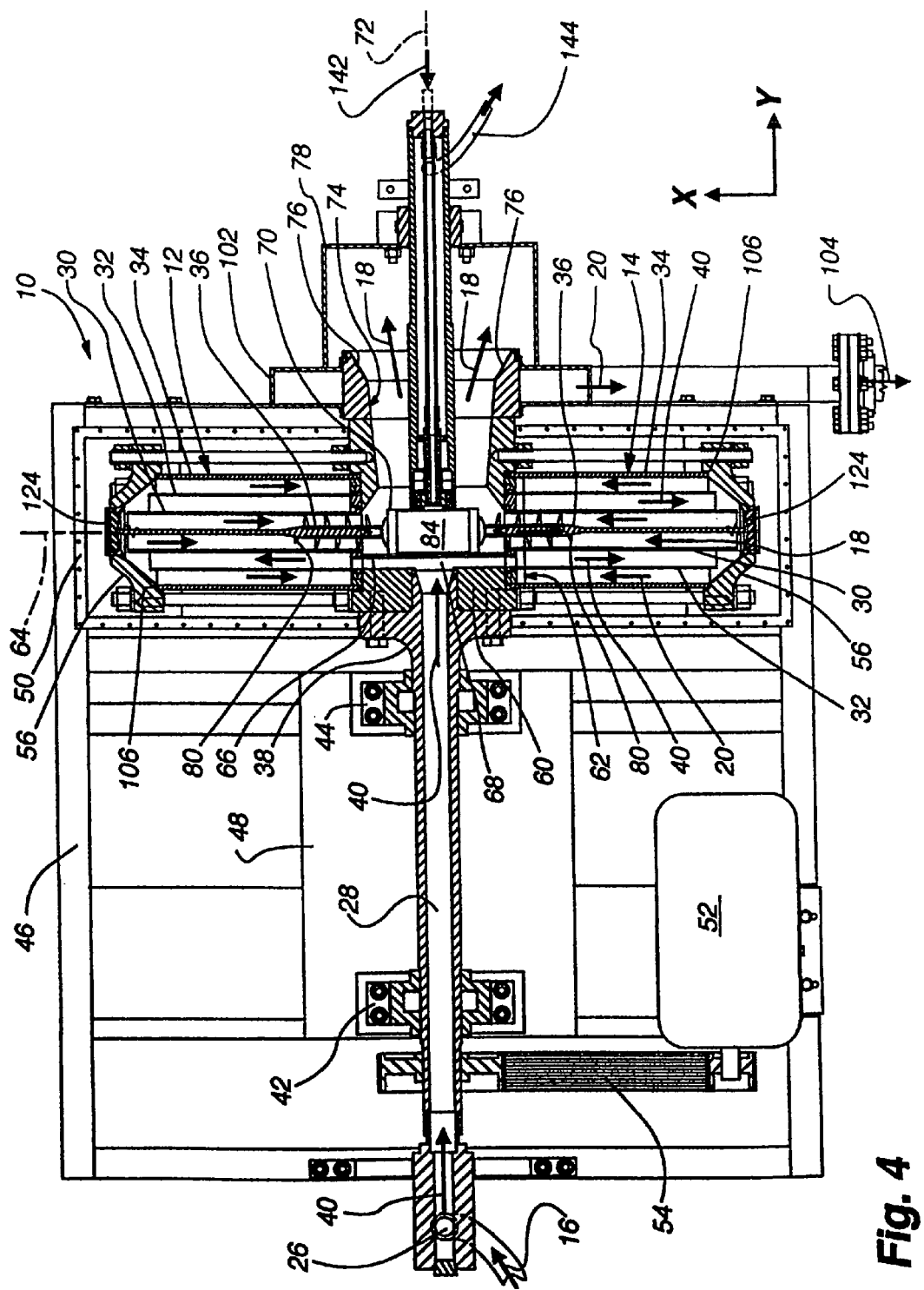
FIG. 4 is a top section view taken along the line 4—4 of FIG. 2, this view showing how the left-hand and belt driven end of the hollow drive shaft cantilever-supports the centrifuge's rotating arm assembly by way of two frame-mounted bearings, this view also showing the centrifuge's input flow path, the flow paths that exist within the rotating arm assembly, the light-product output flow path, the heavy-product output flow path, and hydraulic-fluid input and output flow paths that power a centrally located hydraulic motor that drives two heavy-produce output conveyer screws that are within the rotating arm assembly.

With particular reference to FIGS. 1 and 4, centrifuge 10 in accordance with the invention operates to continuously separate large volumes of an input mixture 16, such as waste water, oil well drilling fluids, etc., that generally consists of a mixture of a light material 22 and a heavy material 24. In the operation of centrifuge 10, the input mixture 16 enters the centrifuge at 26, light material 22 exits the centrifuge at 104, and heavy material 24 exits the centrifuge at 82.

Centrifuge 10 includes at least two laterally opposed and axially aligned rotating-arms 12 and 14 that extend perpendicularly outwardly from one end 38 of a hollow drive shaft 28. The internal volume of drive shaft 28 carries input mixture 16 from input end 26 to the inner ends of arm assemblies 12, and 14.

The opposite end portion 26 of drive shaft 28 into which input mixture 11 is introduced is bearing-supported by two shaft-bearings 42 and 44 that are mounted on and supported by a rectangular frame 46 and its generally centrally located flat plate 48. A relatively large annular housing 50 is also supported by frame 46. Housing 50 surrounds, protects, and contains the centrifuge's rotating arm assembly 12, 14.

Drive shaft 28 and its end-supported arm assembly 12, 14 are driven by an electric motor 52 that is mounted on frame 46. Motor 52 and its drive belt 54 cause drive shaft 28 to continuously rotate in one direction about a rotational or Y-direction axis 24 that is coincident with the center of drive shaft 28. Rotation of drive shaft 28 develops the centrifugal forces that are necessary for material separation.

While physical dimensions are not a limitation on the spirit and scope of the invention, centrifuge 10 is relatively large. For example, the total length of rotating arm assembly 12, 14 may be in the range of from 7 to 8 feet, the diameter of each arm 12, 14 may be in the range of from 1 foot to 1.5 feet, and the rotational speed of shaft 28 may be about 3000 revolutions per minute (RPM). In addition, in an embodiment of the invention, but without limitation thereto, the centrifuge's frame 46 occupies a horizontal plane, and a lower portion of housing 50 may extend below ground level.

Figure 5:
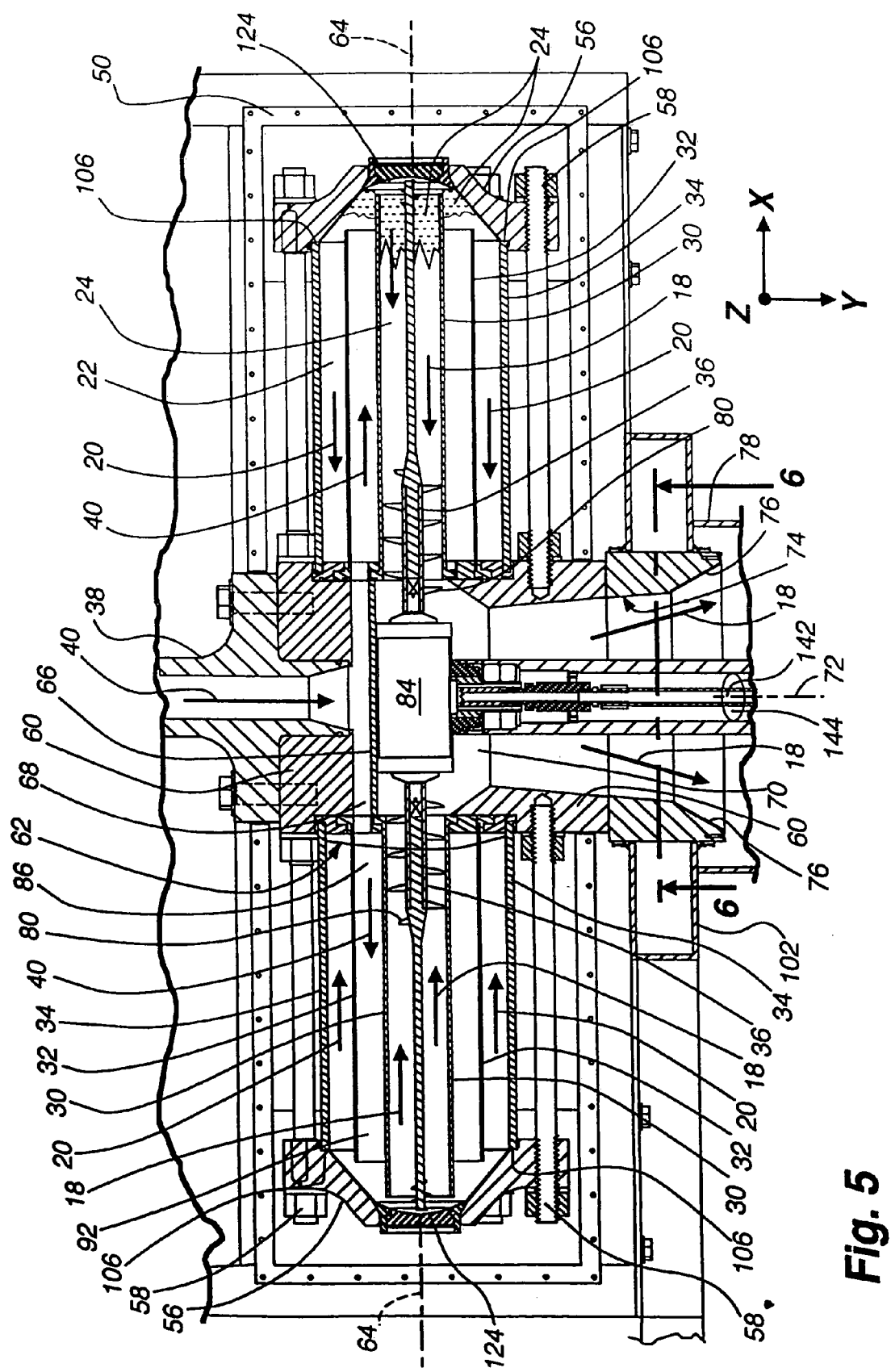
FIG. 5 is an enlarged section view similar to FIG. 4, this view better showing the construction and arrangement of a centrally located and manually removable plug that is contained within a bell-shaped end cap that establishes the outer end of each rotating arm within the rotating arm assembly.
Figure 10:
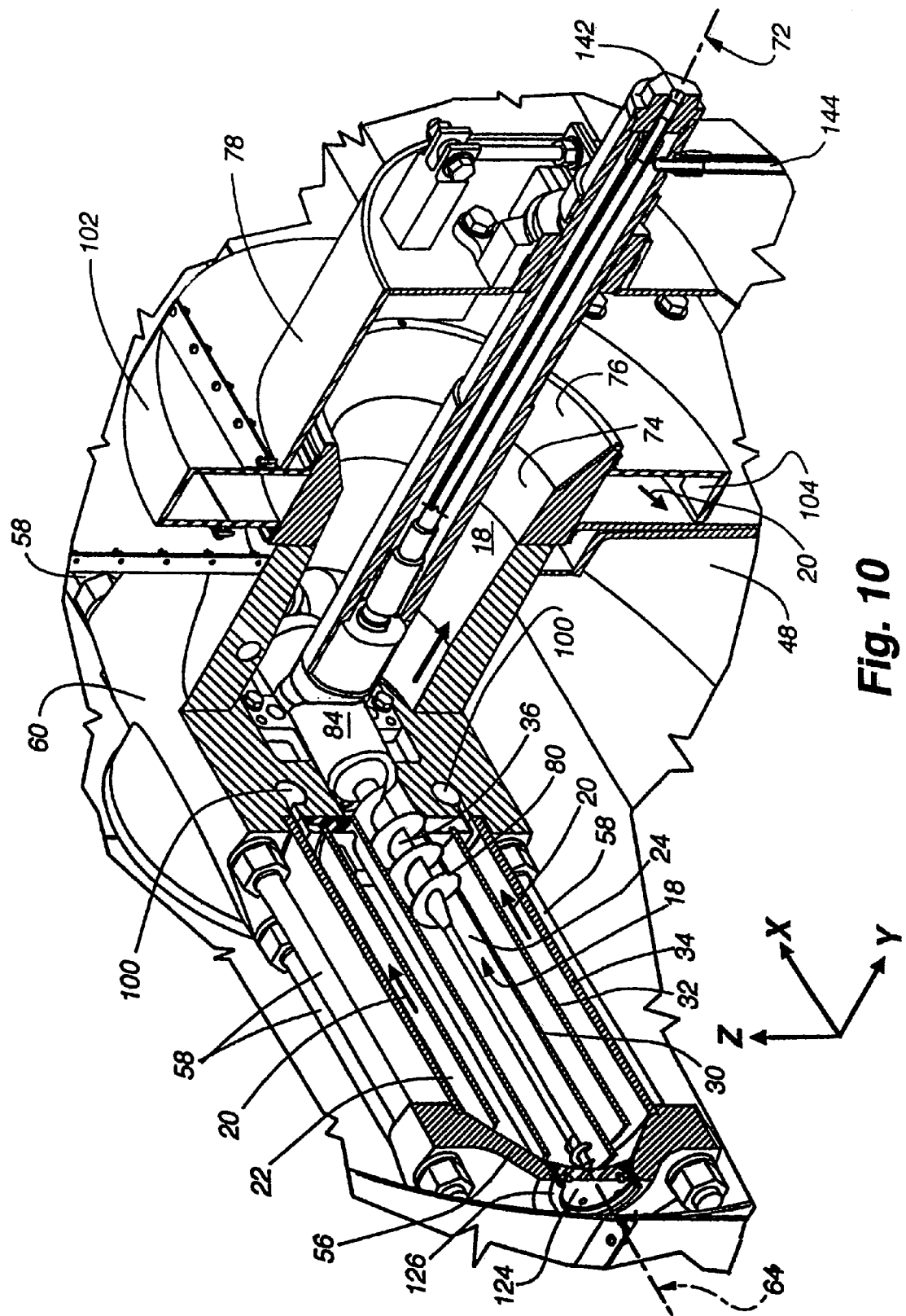
FIG. 10 is a view similar to FIG. 9 wherein the construction and arrangement of one of the two arms is better seen.

With particular reference to FIGS. 4, 5 and 10, each of the two tubular-shaped arms 12, 14 has a generally cylindrical shape and are of generally the same construction. Each of the arms 12, 14 includes a cup-shaped end cap 56, an innermost tube 30, an intermediate tube 36 and an outermost tubular housing 34. Seven parallel and radially extending metal bolts 58 have their inner ends threaded into a centrally located central member 60 that is bolt-attached to the end 38 of drive shaft 28. The outer ends of bolts 58 are nut-attached to end cap 56.

While the radial spacing between the tubes can be any distance depending on the application, the radial spacing between tubes 30, 32, 34 is approximately from about 1 inch to about 4 inches, preferably 1.9 inches, and the axial lengths of tubes 30, 32, 34 can be any of a variety of different lengths that maintain outer tube 34 as the shortest tube, that maintain intermediate tube 32 as an intermediate length tube, and that maintain inner tube 30 as the longest tube. The tubes can be made of any material that has sufficient strength to withstand the forces of the centrifuge, such as but not limited to, metal or plastic.

The length of innermost tube 30 is preferably adjustable. The outer end can include a sleeve portion (not shown) that slides along the length of the rest of the tube to allow length adjustment. The sleeve portion is fixed to the rest of the tube 30 by a set screw, or other attachment mechanism. This allows for a fine adjustment of length of the innermost tube 30 without having to replace the entire tube 30. This can be helpful to match the tube to the plug size, as is discussed in more detail below.

While all three of the tubes 30, 32, 34 are rigid tubes that have a circular cross section, it is preferred that outer tubular housing 34 be made of a thicker or a stronger material than are tubes 30 and 32. In accordance with the invention, inner tube 30 is a relatively longer tube that has a relatively small diameter, intermediate tube 32 is a relatively shorter tube that has a relatively larger diameter. The three tubes 30, 32, 34 are mounted such that their inner ends occupy a common flat plane 62 (shown in FIG. 4 as a Y-Z plane), and the three tubes 30, 32, 34 are concentric tubes that are centered on centrally located arm axis 64.

Figure 6:
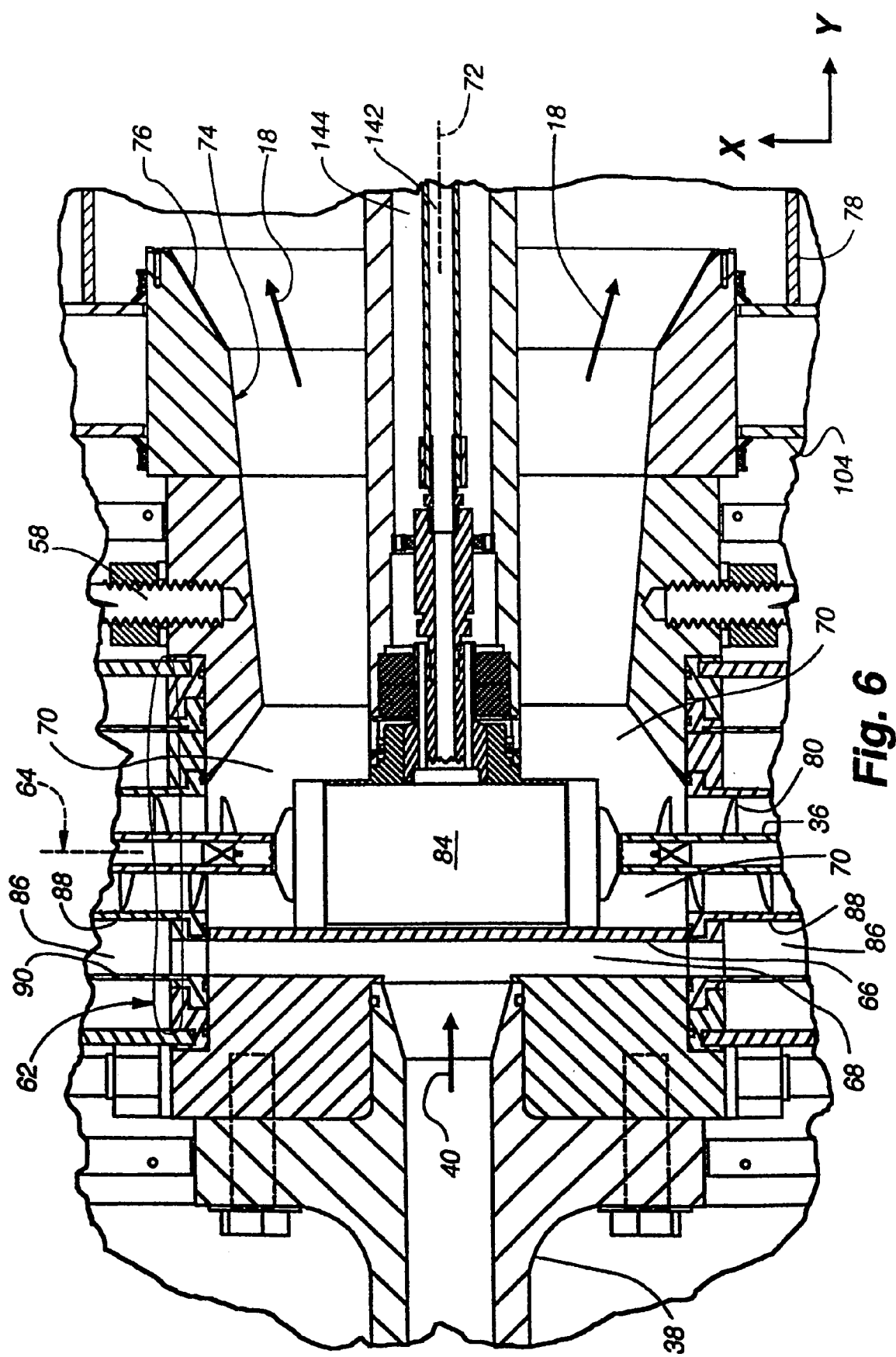
FIGS. 6 and 6A are enlarged section views of the central portion of the centrifuge as shown in FIG. 5, this view better showing the construction and arrangement of the base portions of the three concentric tubes that are cantilever-supported within each arm of the centrifuge's rotating arm assembly.

As perhaps best seen in FIGS. 4, 5 and 6, centrally located driven main body member 60 includes a dividing wall 66 that forms an input mixture chamber 68 on one side thereof and a heavy material output chamber 70 the other side thereof.

Each of the innermost and axially aligned tubes 30 contains a conveyer screw or auger 36 that aids in the removal of heavy material 24 that builds up at end-cap ends 56 of arms 12, 14 during use of centrifuge 10 to separate light material 22 from heavy material 24, both materials being contained within input mixture 16. The heavier material 24 builds up to form a plug around the end of the innermost tube 30 and covers a portion of the end cap 56. Conveyor screws 36 rotate about the central axis 64 of arms 12, 14 and aid in the movement of heavier material 24 radially inward and through innermost tube 30 toward the centrifuge's axis of rotation 72, whereas the heavier material 24 enters the heavy output chamber 70 within driven member 60. This heavy material 24 then moves out of centrifuge 10 by way of an exit cone 74 that is formed about rotational axis 72.

The apex of cone 74 lies on rotational axis 72, and its broad base 76 terminates at an X-Z plane that is within a small-size annular housing 78. The conveyor screws 36 can have different flighting 80 designs on them to facilitate the removal of the heavier material. As shown, the flighting 80 at the outer ends of the arms 12, 14 is small and extends for a short distance, for example 6 inches, to assist in breaking up the compacted heavier material 24 and help it begin moving toward the exit cone 74. The middle length of the conveyor screw 36 preferably has no fighting, as the heavier material 24 is pushed to some point there along by the head pressure created by the spinning of the centrifuge 10. The inner end of the conveyor screws are flighted 80 to help pull the heavy material 24 towards the exit 82, and push it through the change of direction in the transition between the inner end of the inner tube 30 and the exit cone 74. The length of the flighting preferably extends a distance that meets the heavy material once the head pressure is no longer sufficient to advance the heavy material through the inner tube 30.

Figure 11:
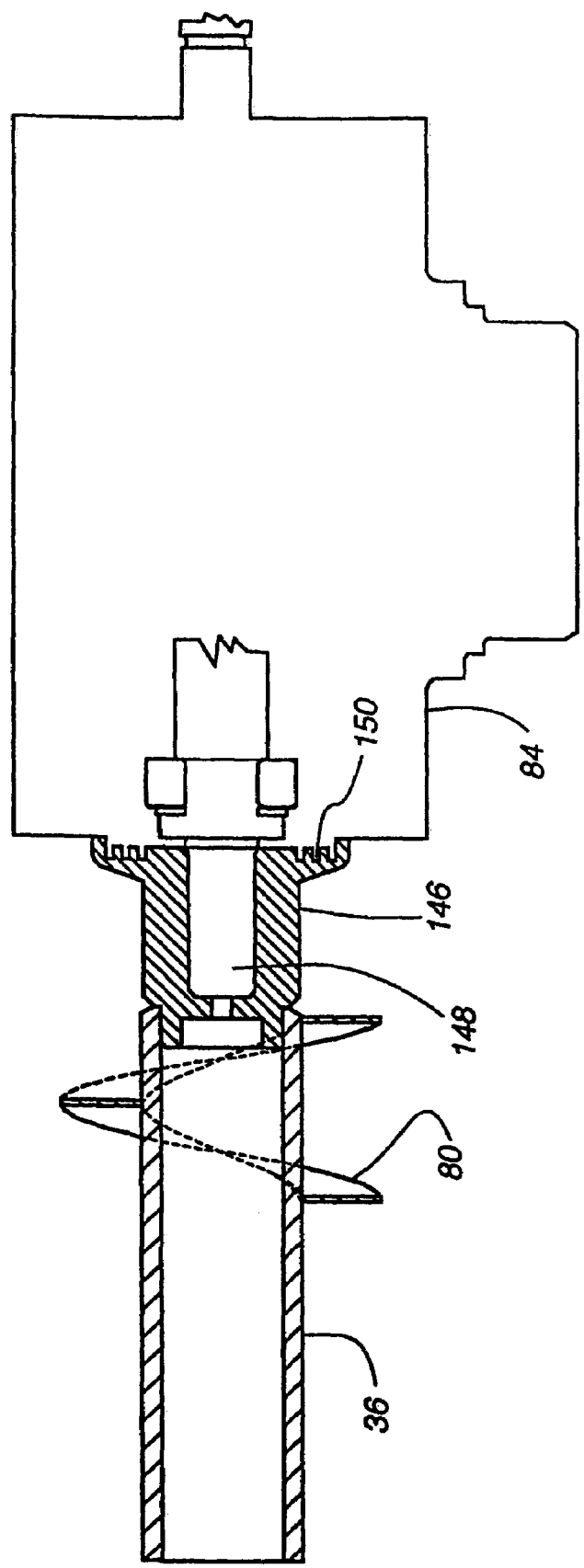
FIG. 11 is a view that shows how one of the inner ends of the two heavy material output augers are connected to opposite sides of the centrally located hydraulic motor.

In a preferred embodiment of the invention, and as shown in FIG. 11, the inner ends of the conveyer screws 36 are cantilever-mounted to opposite sides of a centrally located hydraulic motor 84. However, within the spirit and scope of the invention, the outer ends of conveyer screws 36 may be bearing-supported, as by the use of bearings (not shown) that are carried by outer tube-housing 34 or by end cap 56.

Input mixture 16 moves through the hollow center of shaft 28 and along rotational axis 72 as arm assembly 12, 14 rotates about axis 72. Input mixture 16 then enters input chamber 68 within driven member 60. As best seen in FIG. 6, chamber 68 communicates with a cylindrical-shaped volume 86 that is formed by the outer surface 88 of innermost tube 30 and the inner surface 90 of intermediate tube 32. Input mixture 16 now moves radially outward and through cylindrical-shaped volume 86 to the distal end 92 of volume 86. At the location of end cap 56, input-mixture flow 16 separates into a heavy-material flow 24 and a light-material flow 22.

Heavy-material flow 24 first compacts at the end of the arms 12, 14 and moves radially inward through innermost tube 30, this flow 24 being assisted by conveyor screw 36, enters chamber 70, enters exit cone 74, and then enters housing 78 wherein the heavy material 24 exits centrifuge 10 at 82 as best shown in FIG. 1.

As perhaps best seen in FIG. 8, light-material flow 22 concomitantly moves radially inward through a cylindrical volume 94 that is formed by the outer cylindrical surface 96 of intermediate tube 32 and the inner cylindrical surface 98 of outer tubular housing 34. At the radially inward end of volume 94, light-material flow 22 enters passageways 100 that are formed in the metal walls of cone 74. By way of passageway 18, light-material flow 22 enters the intermediate size annular housing 102 whereat light-material flow 22 exits centrifuge 10 at 104 as best shown in FIG. 1.

As input mixture 16 is forced to the distal ends of arms 12, 14 by the rotation of the arm assembly about axis 72, the solid or heavy material 24 that is within input mixture 16 compacts or compresses to form a plug of heavy material 24 adjacent to and abutting the inside surface of end cap 56. As a result, light-material flow 22 is forced back toward the center of rotation 72 in the outer tube 32. As this plug of heavy material 24 builds up in size, heavy-material flow 24 is also forced back toward the center of rotation 72 in the inner tube 30.

More particularly, at the distal end of each of the two arms 12 and 14, the end of long-tube 30 extends beyond the end of shorter-tube 32. As solids are deposited at the distal end of arms 12 and 14 a relatively solid plug of heavy material 24 is formed, this plug increases in thickness, along arm axis 64, until such time as the plug seals the end of long-tube 30. However, this plug thickness parameter does not increase enough to seal off the end of shorter tube 32. Thus, the plug partially defines the boundary of the two output flow paths 18 and 20.

The thickness of the plug is regulated in part by the action of conveyer screw 36. While not a limitation on the spirit and scope of the invention, the elongated shaft of conveyor screw 36 does not have fighting or threading 80 along its entire length, but preferably has flighting 80 only adjacent to its inner end, as best shown in FIG. 5, and described above.

Centrifugal forces on the heavy material 24 at the distal end of arms 12, 14 combined with the hydrostatic head of the overlying liquids and solids and assist in forcing the solids 24 through flow path 18, in a direction toward the center of rotation 72. The distance that solids 24 move inward through tube 30 depends on the operating parameters of centrifuge 10 (for example the moment arm and the RPM), and on the type of input mixture 16 that is provided to centrifuge 10. Usually, solids within input mixture 16 require the assistance of flighting 80 on conveyor screw arm 36 to move the solids along flow path 18. It is possible, however, to have an input mixture 16 with a heavy material content that does not require the presence of conveyor screws to assist the heavy material through the inner tube towards the exit cone 74.

The thickness of the heavy-material plug that forms at the distal end of each arm 12, 14 is determined by an equilibrium condition that is established by the growth of the plug and the removal of the plug by way of flow path 18 through the inner tube 30. Basically, the amount of flighting 80 adjacent to the inner end of conveyor screw 36 determines the equilibrium size of the plug. Assuming an input flow 16 having relatively constant amounts of heavy 24 and light materials 22, a greater amount of flighting 80 reduces the equilibrium plug size, whereas less flighting 80 increases the equilibrium size of the plug. This relationship is due to the effect that flighting 80 has on the removal of the heavier material 24 by way of flow path 18.

The plug size is preferably at least at a minimum size or radial thickness to insure that the plug contacts only the ends of the inner tubes 30 that define the input flow path 40, the light-material output flow path 20, and the heavy material output flow path 18. This plug size should be relatively conservatively designed to accommodate a temporary reduction in the amount of heavy material 24 within input mixture 16 (which reduction would cause the size of the plug to grow more slowly). If the heavier/lighter material composition of input mixture 16 is to be changed for more than a temporary period, such as when a different type of input mixture 16 is to be separated, the length of flighting 80 that is provided on conveyer screw 36 may require modification to accommodate this change. This modification is accomplished by removing an existing conveyer screw 36 and replacing it with a conveyer screw having a different fighting configuration 80. Other changes may also need to be made, such as changing the RPM of the centrifuge or the length or spacing of the tubes 30, 32.

An important feature of the present invention is a mechanical interlocking construction and arrangement within the two arm assemblies 12, 14 that enables the arm assemblies to be easily cleaned, to be easily repaired by the selective replacement of components that make up the arm assemblies, and to be easily modified, for example in order to change the separation characteristics of centrifuge 10 to in order to accommodate a change in input mixture 16.

Figure 6A:
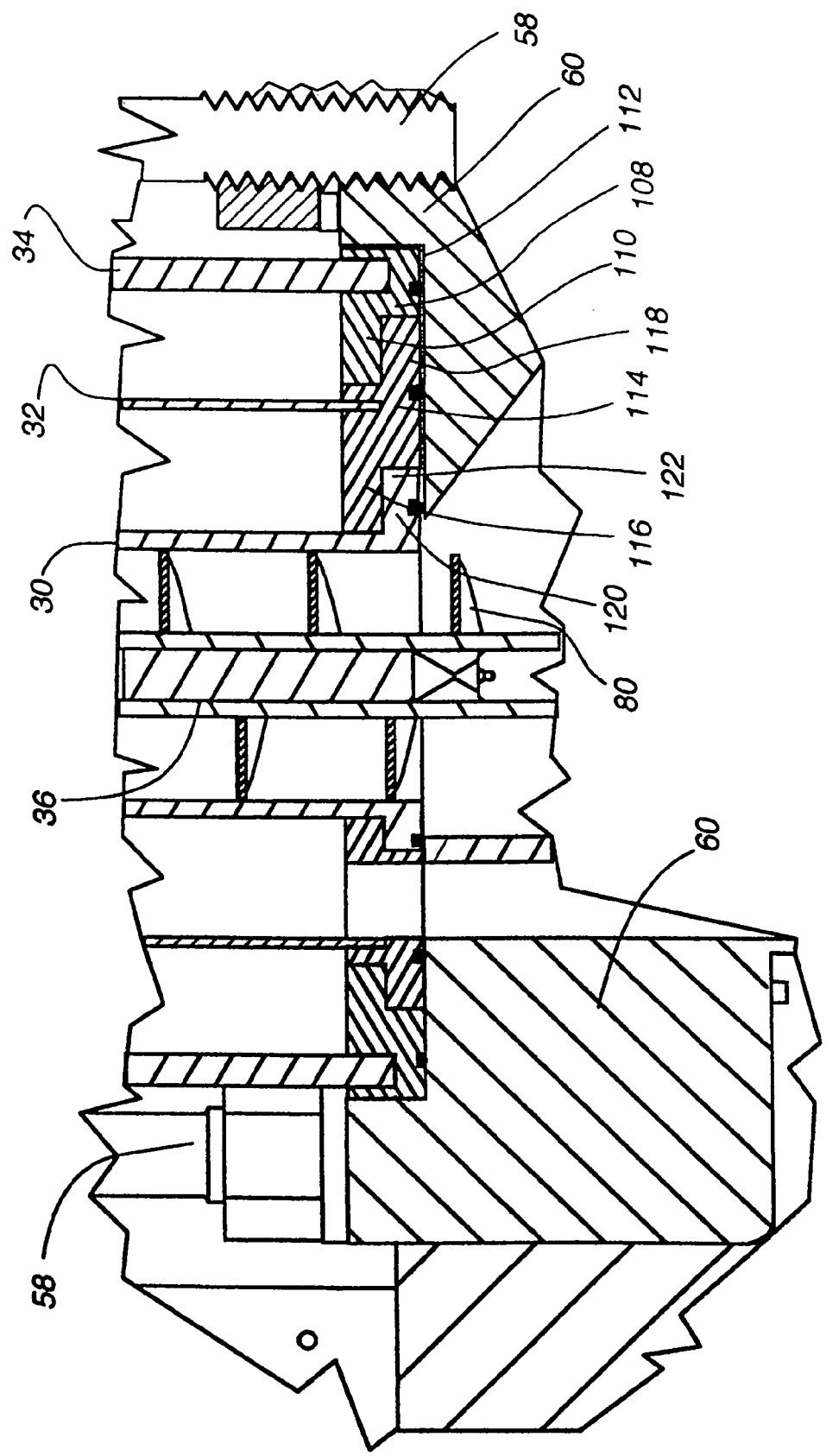
Figure 9:
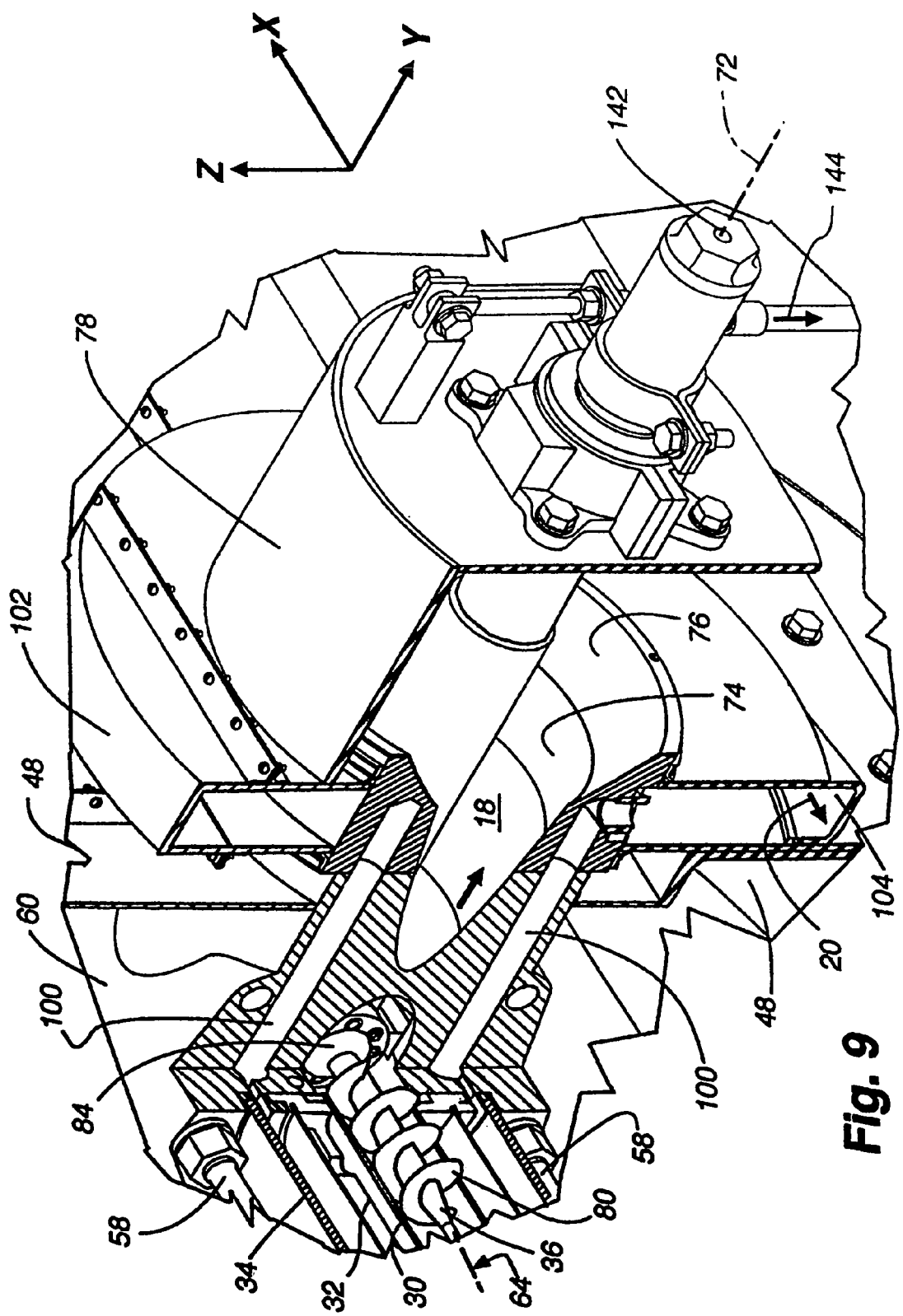
FIG. 9 is a partial section, top and right side perspective view of the centrifuge, this view also showing two of the four flow paths by which the heavy material output flows to the small-size annular housing shown in FIG. 1.

With particular reference to FIGS. 5, 6 and 6A, when bolts 58 are tightened, end cap 56 and housing tube 34 operate to securely mount tubes 30 and 32 to centrally located main body member 60. While only the circular outer end of the outer housing-tube 34 is physically engaged by a corresponding circular portion of end cap 56, as is shown at 106 of FIG. 5, the radially inward force that is applied to housing-tube 34 when bolts 58 are tightened securely mounts housing-tube 34 to driven member 60.

By virtue of a mechanical interlocking arrangement in accordance with the invention, this radially inward force that is thus produced by housing-tube 34 when bolts 58 are tightened also securely mounts intermediate tube 32 and inner tube 30 to driven member 60 in a cantilever manner.

More specifically, and with particular reference to FIGS. 6 and 6A, but without limitation to the specific details thereof, the end of tube housing 34 that is generally adjacent to rotation axis 72 integrally carries a first annular ring 108 having an overhanging ring portion 110. The ring 108 is seated in and sealed with a circular depression 112 in the main body member 60.

In addition, the corresponding end of intermediate tube 32 integrally carries a second annular ring 114 having an overhanging ring-portion 116, and having a ring portion 118 that underlies the overhanging ring portion 110 that is carried by housing-tube 34. Thus, when housing-tube 34 is secured to main body member 60 by operation of bolts 58, overhanging ring-portion 110 operates to physically trap the underlying-ring portion 118 of intermediate tube 32, thus securing intermediate tube 32 to driven member 60.

In addition, the corresponding end of inner tube 30 integrally carries a third annular metal ring 120 having an underlying ring-portion 122. When intermediate tube 32 is secured to driven member 60 as above described, overhanging ring-portion 116 that is carried by intermediate tube 32 operates to physically trap the underlying-ring portion 122 of inner tube 30, thus securing inner tube 30 to driven member 60.

In operation, should it become necessary to repair, service and/or modify arm assemblies 12, 14, all that need be done is to remove bolts 58, disassemble the arm assemblies by removing the end caps 56 and tubes 30, 32, 34, perform the needed operations, and then reassemble the arm assemblies 12, 14.

When new and/or different tubes 30, 32, 34 are to be placed within centrifuge 10, the old tubes are removed and the new tubes are placed within the arm assemblies 12, 14, the new tubes corresponding to the old tubes in the manner in which they are mounted to driven member 60 as above described.

Figure 3:
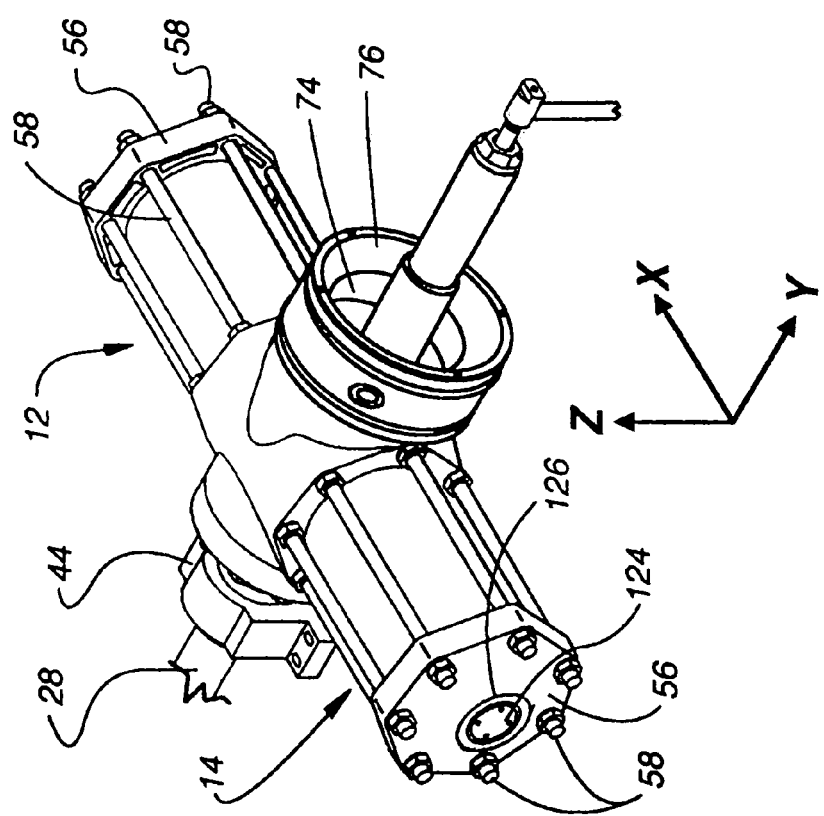
FIG. 3 is a top and right side perspective view of the rotating arm assembly that is contained within the relatively large annular housing of FIG. 1.
Figure 2:
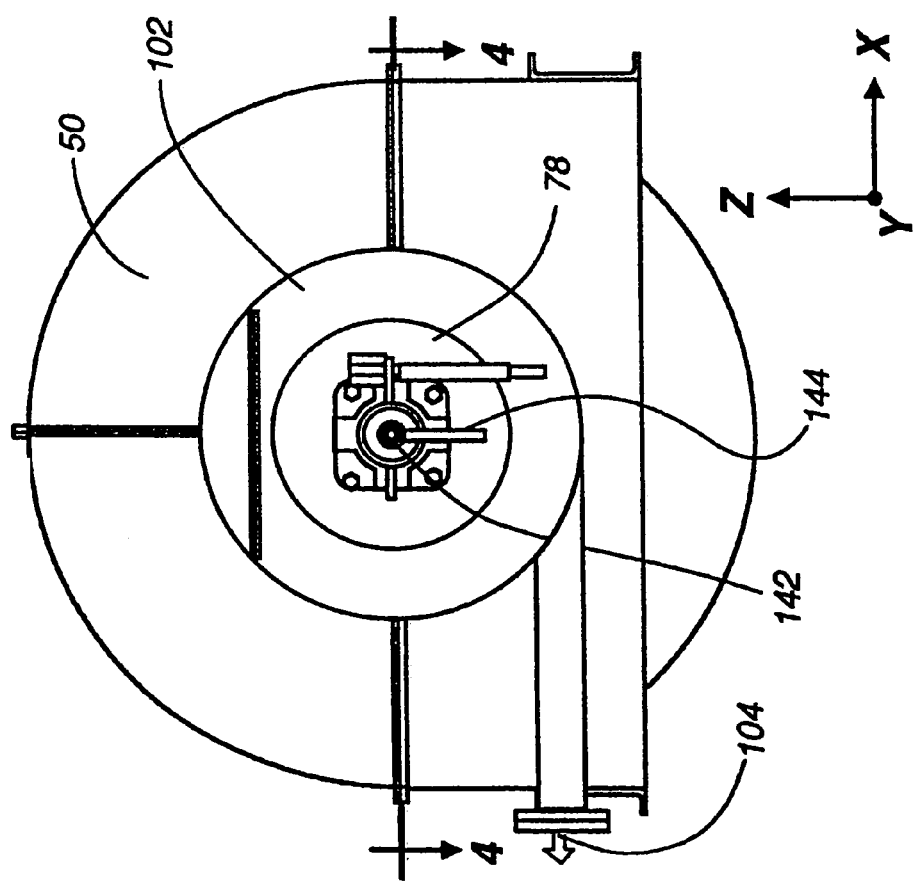
FIG. 2 is a right side plan view of the centrifuge of FIG. 1.
Figure 12:
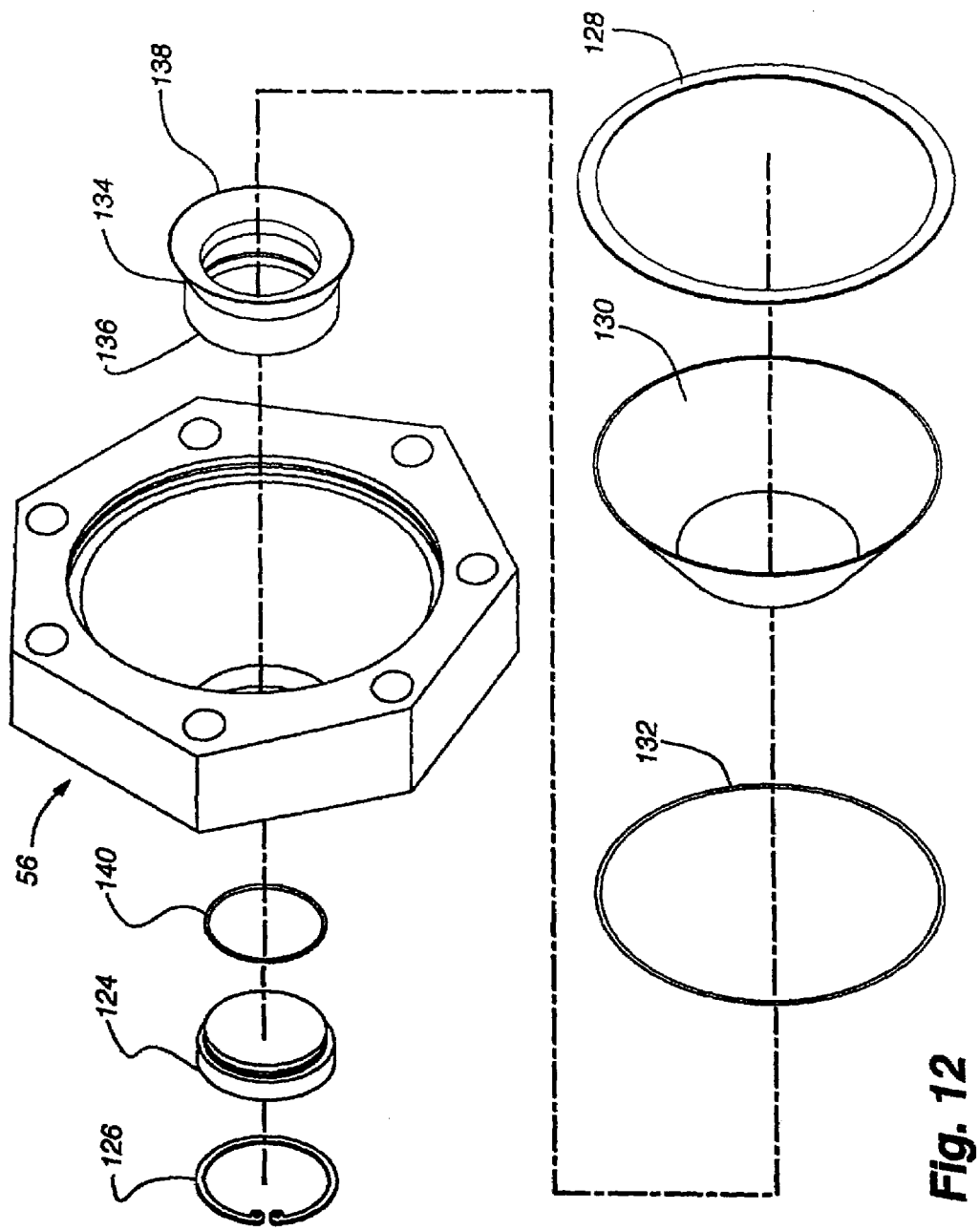
FIG. 12 is a view that better shows the snap ring construction of the removal plug that is contained within the bell-shaped end cap that establishes the outer end of each rotating arm within the rotating arm assembly.

With particular reference to FIGS. 3, 5 and 12, in accordance with a feature of the invention the center of each of the two arm end caps 56 includes a manually removable plug 124 that is press-fit within end cap 56 and secured in place by operation of a manually removable C-ring 126. Manual removal of C-ring 126 and then plug 124, enables the cleaning/flushing of the distal end of arms 12 and 14, and may also provide for the replacement of conveyer screws 36. Removal can be effected by unscrewing the threaded collar 146 from the output shaft 148 of the hydraulic motor 84. The end cap 56 also includes a first seal 128 positioned between the end cap 56 and the annular end of the tubular housing 34. A semi-conical liner 130 protects the inner wall of the end cap 56 from damage. The liner 130 can be made of metal, plastic or another material that can withstand the intense pressure and conditions in the centrifuge. A second seal 132 is positioned between the liner 130, end cap 56 and annular end of the tubular housing 34. A plug collar 134 having a circular cylindrical top end 136 and an outwardly sloping semi-conical bottom end 138 is inserted into the end cap 56 from the inside so the bottom end 138 engages with the inner conical walls of the end cap 56. This engagement (see FIG. 5) keeps the plug 124 securely positioned in the end cap 56 without risk of the plug 124 exiting through the aperture formed in the end of the end cap 56. The plug collar 134 extends beyond the end of the end cap 56, and defines an annular groove around its inner diameter to receive the snap-ring collar 126. A third seal 140 fits between the plug 140 and the plug collar 134.

With particular reference to FIG. 4, the dividing wall 66 that divides driven member 60 into input chamber 68 and heavy-material output chamber 70 also operates to physically mount a hydraulic motor 84 at a generally central location within output chamber 70 and generally on the centrifuge's rotational axis 72. Hydraulic motor 84 contains a single rotating member (not shown) that rotates on arm-axis 64, and that mounts the inward ends of the two conveyor screws 36, as is best seen in FIG. 11. An input hydraulic line 142 and a concentric output hydraulic line 144 provide variable power to hydraulic motor 84, and thus variable speeds of rotation for the two conveyor screws 36.

As shown in FIG. 11, the conveyor screw is mounted to a threaded collar 146. The threaded collar is then mounted to the output shaft 148 of the hydraulic motor 84. The threaded connection is preferably such that when the centrifuge 60 and auger screws 36 are in operation, the collar is biased towards the hydraulic motor 84. An annular bearing 150 is provided between the hydraulic motor and the threaded collar to keep contaminants away from the output shaft 148 and ensure that the auger screws keep spinning during operation.

Another important feature of the present invention is the construction and arrangement whereby the speed of rotation of arm assembly 12, 14 can be varied independent of the speed of rotation of the conveyor screws 36 that are within each of the two arms 12, 14. For example, but without limitation thereto, this unique two-motor construction of centrifuge 10 enables the speed of motor 52 to be varied as a function the centrifugal force that is required to separate a given input mixture 16, whereas the speed of motor 84 can be independently varied as a function of the amount of heavy material 24 that is within a given volume of the given input mixture 16.

As perhaps best seen in FIG. 6, concentric hydraulic lines 142, 144 are generally linear lines that extend generally coincident with the central axis of output cone 74 and the centrifuge's rotational axis 72. Hydraulic motor 84 rotates, while lines 142, 144 are stationary. Well-known rotary seals are provided to make a connection from lines 142, 144 to motor 84.

There are several benefits gained by a centrifuge 10 constructed and arranged in accordance with the present invention. The concentric tubular rotating arms 12, 14 of the present invention provide an extremely long residence time during which an input mixture is subjected to centrifugal separating forces. The longer this residence time, the larger the amount of heavy material 24 that is removed from the input mixture. In addition, heavy material 24 is deliquefied by means of the compaction that occurs at the distal ends of the centrifuge's rotating arm assemblies 12, 14. The centrifuge arm assemblies 12, 14 are easily disassembled for maintenance, part replacement, and/or performance modification. A centrifuge 10 in accordance with the present invention generates tremendous centrifugal force in a machine having a relatively small physical size, and the centrifuge can be easily adjusted to handle a wide variety of input materials and flow rates. Since two separate drive means 52, 84 are provided, the rate of arm rotation and the rate of removal of the heavy material 24 from the centrifuge 10 can be independently varied, and removal of heavy material 24 from the centrifuge 10 is by way of a relatively large exit cone 74.

Figure 13:
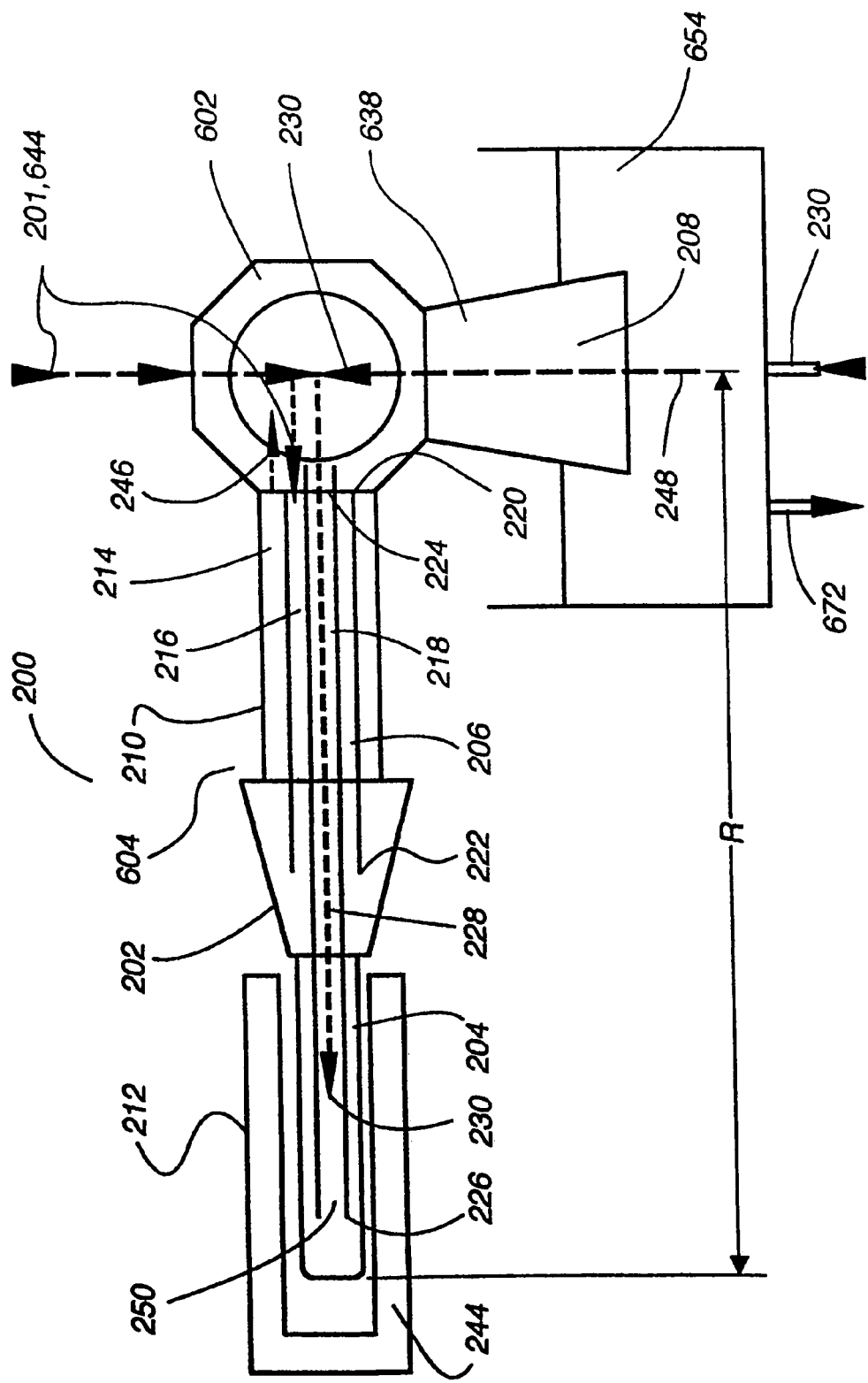
FIG. 13 is a side section diametric view of a centrifuge and centrifuge arms and reactor zones.
Figure 14:
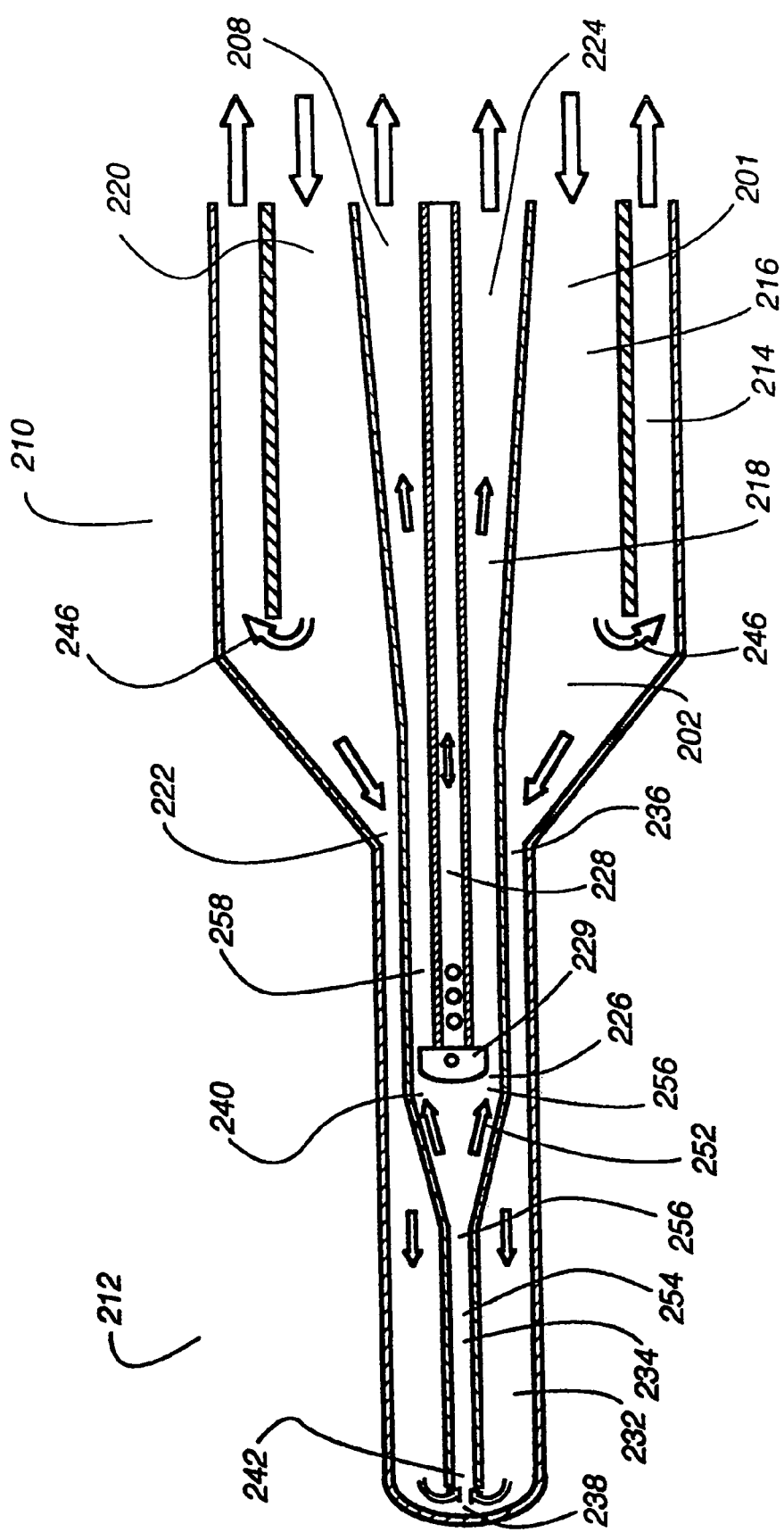
FIG. 14 is an enlarged view of the sludge thickening and reaction zone portions of the centrifuge arm.

The centrifuge of the present invention can be utilized as an oxidation reactor with some structural modifications. The wet oxidation centrifuge reactor disintegrates waste containing sludge in a supercritical oxidation reaction. A centrifuge is used to house the supercritical oxidation reaction to create a more efficient environment for generating supercritical conditions (i.e., high pressure, high temperature). The influent is typically in the form of a sludge slurry injection. After undergoing the oxidation reaction, the resulting effluent is comprised of ash, $CO_2$, and $H_2O$, and other by-products depending on the constituents of the incoming slurry. FIG. 13 provides a schematic overview of the various process zones and related reactor parameters for an embodiment of the supercritical wet oxidation centrifuge reactor. FIG. 14 is an enlarged view of the centrifuge arm in FIG. 13 and includes additional details regarding the geometry and configuration of the arm internal portions.

Several identifiable zones exist within the centrifuge reactor 200 during processing. Referring to FIGS. 13–14, generally the influent first enters an entry zone, next a sludge thickening zone 202, then an oxidation reaction zone 204, next a cooling zone 206, and finally an exit zone. Tables 1–2 herein and FIGS. 15 through 18 both list and illustrate examples of the supercritical wet oxidation centrifuge reactor parameters. The key reactor parameters are pressure, specific volume, velocity, and temperature, which all provide insight into the reaction process occurring within the various reactor zones. The following provides a general overview of the centrifuge structure and specific details with respect to the centrifuge reactor parameters.

Figure 22:
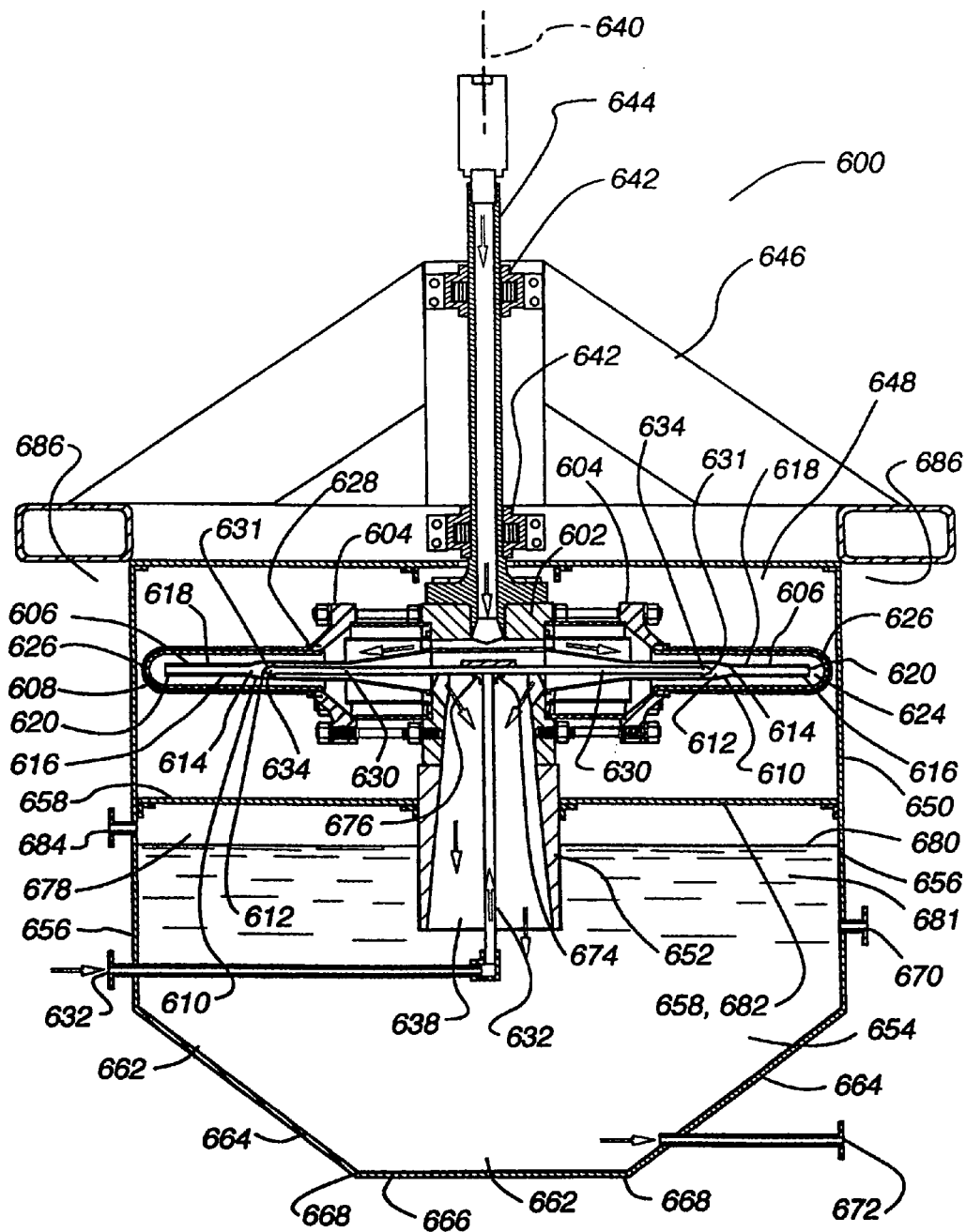
FIG. 22 shows another embodiment of the centrifuge of the present invention configured for use as an oxidation reactor, including a frame for suspending the reactor and a tank for receiving the oxidation reaction by-products.
Figure 23:
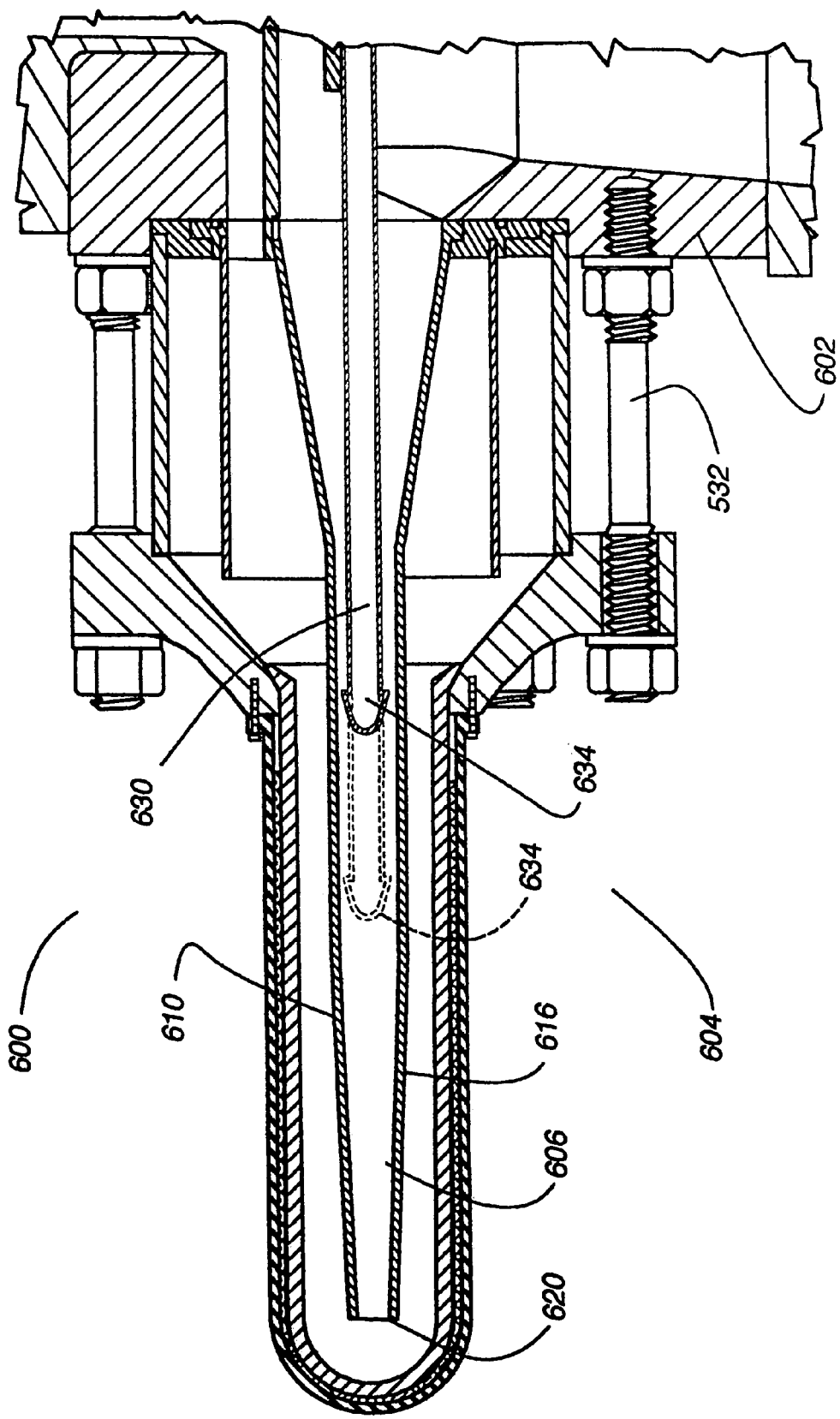
FIG. 23 is an enlarged view of one of the arms of the oxidation reactor shown in FIG. 22.

Referring to FIGS. 22 and 23 as representative of a preferred embodiment for this discussion, the oxidation centrifuge 660 generally includes a main body portion 602 and at least two centrifuge arms 604 extending from the main body portion 602. The main body portion 602 is suspended from a framing portion 646 and includes a bottom portion 652 that extends into a discharge chamber 654 or tank. The discharge chamber 654 serves as the base portion of the centrifuge reactor 200. In operation, the main body portion 602 and arm portions 604 rotate about a vertical axis 640 through the center of the main body portion 602. Both an influent manifold 644 and an effluent manifold 638 are formed in the top 648 and bottom center portions, respectively, of the main body portion 602. The centrifuge arms 604 are in communication with the influent 644 and effluent 638 manifolds.

The centrifuge arms include a beginning portion 210 and an end portion 212. The centrifuge arm beginning portion 210 includes three concentric tubes that define three concentric channels. The outer channel 214 (or outer annular region) is in communication with the effluent manifold 638, the middle channel 216 (or intermediate annular region) is in communication with the influent manifold 644, and the center channel 218 (inner tube) is in communication with the effluent manifold 638. In an alternate embodiment, the outer channel 214 may be in communication with a centrate outflow channel (not shown) or port or no outer channel 214 may be present. The outer channel 214 generally has a consistent cross-sectional area. The middle channel 216 cross-sectional area increases from the end 220 nearest the main body 602 portion to the center portion of the middle channel 216 and then decreases from the center portion to the end 222 nearest the end portion of the centrifuge arm. The center channel cross-sectional area decreases from the end 224 nearest the main body portion to the end 226 nearest the end portion of the centrifuge arm 604.

Central to the center channel is a cooling tube or probe 228. The probe 228 introduces cooling water 230 to the center channel. The probe 228 is connected to a cooling water supply pipe 230 that extends from the side of the discharge chamber and up the center of the effluent manifold 638. The probe(s) 228 extend outwardly from the center of the effluent manifold 638 into the center of the center channel 218. The probes 228 can be mutually or independently adjustable and can also be configured to automatically adjust depending on the pressure in the center channel 218.

The end portion 212 of the centrifuge arm 604 includes two concentric tubes that define two concentric chambers: an outer chamber 232 and an inner chamber 234. The outer chamber 232 is in communication with the middle channel 216. The inner chamber 234 is in communication with the center channel 218. The outer chamber 232 is also in communication with the inner chamber 234. The outer chamber 232 cross-sectional area increases from the end 236 nearest the main body portion 602 to the opposite end 238. The inner chamber 234 cross-sectional area decreases from the end 240 nearest the main body portion 602 to the opposite end 242. The probe 228 extends from the middle channel 216 into the inner chamber 234 and acts a plunger to partially block and control the flow of effluent from the inner chamber 234 to the middle channel 216.

A flow path is defined through the main body portion 602 and centrifuge arm 604 during operation of the centrifuge reactor 200. The influent sludge slurry injection enters the influent manifold 644 at the top of the centrifuge main body 602 and flows down to openings defined by the centrifuge arm middle channels 216. The forces exerted by the rotation of the centrifuge 200 causes the slurry to enter the middle channels 216. The influent slurry flows along the middle channel 216 to the beginning of the outer chamber 232 on the end portion 212 of the centrifuge arm 604. The area from the beginning of the influent manifold 644 to the beginning of the outer chamber 232 on the end portion 212 of the centrifuge arm is known as the entry zone 201.

Centrate 246 flows out of the middle channel 216, into the outer channel 214, and back into the effluent manifold 638 in the center of the main body portion 602 (centrate is the resulting separated liquid from a centrifuge process). In alternate embodiments, the centrate 246 may exit the centrifuge 200 via a centrate port (not shown) or no outer channel may be present. In the middle channel 216, the influent begins to thicken. This area is known as the sludge thickening zone 202.

The influent continues into the outer chamber 232 and to the end 212 of the centrifuge arm. The end portion 212 of the centrifuge arm 604 is heated by a heating element 244. The influent/effluent next flows into the inner chamber. The influent sludge is disintegrated in oxidation reactions in the outer 232 and inner 234 chambers. This region is known as the oxidation reaction zone 204.

The oxidized influent (now effluent) mixes with cooling water 230 from the probe 228 and flows into the center channel 218 of what is called the cooling zone 206. The effluent finally flows into the effluent manifold 638 in the center of the main body portion 602. The effluent manifold 638 and surrounding regions are known as the exit zone 208. In some embodiments, the effluent in the effluent manifold 638 mixes with any centrate 246 present and flows down into the discharge chamber 654 at the base of the centrifuge 200. In other embodiments, the centrate 246 may be separately removed from the centrifuge 200 or no centrate 246 is present.

FIGS. 3 through 6 trace the pressure, specific volume, velocity, and temperature versus the centrifuge arm distance (see Table 1 for corresponding data). The graphs illustrate the values of these four parameters taken along the centrifuge arm as the waste sludge makes its way from the influent manifold 644 central to the main body 602 to the end 212 of the centrifuge arm 604 distal to the influent manifold 644 and back to the beginning 210 of the centrifuge arm proximate the effluent manifold 638, where the reactants exit the centrifuge 200.

TABLE 1

| | arm (ft) | temp (deg F.) | spec vol (cu ft/lb) | pressure (psi) | velocity (fps) | time (sec) |
|---|---|---|---|---|---|---|
| THICKENING ZONE | 0.45 | 180 | 0.0165 | 0 | 0.17 | 0 |
| | 0.65 | 180 | 0.0165 | 107 | 0.17 | 1.20 |
| | 0.85 | 180 | 0.0165 | 254 | 0.17 | 2.40 |
| | 1.05 | 180 | 0.0165 | 439 | 0.17 | 3.60 |
| | 1.25 | 180 | 0.0165 | 663 | 0.17 | 4.80 |
| | 1.45 | 180 | 0.0165 | 927 | 0.17 | 6.00 |
| | 1.65 | 180 | 0.0165 | 1229 | 0.17 | 7.20 |
| | 1.85 | 180 | 0.0165 | 1571 | 0.17 | 8.41 |
| | 2.05 | 180 | 0.0165 | 1951 | 0.17 | 9.61 |
| | 2.25 | 180 | 0.0165 | 2371 | 0.17 | 10.81 |
| OXIDATION ZONE | 2.45 | 180 | 0.0165 | 2829 | 0.05 | 12.67 |
| | 2.66 | 734 | 0.0360 | 3155 | 0.11 | 15.36 |
| | 2.87 | 869 | 0.1800 | 3241 | 0.53 | 16.01 |
| | 3.08 | 947 | 0.1900 | 3295 | 0.56 | 16.39 |
| | 3.28 | 1020 | 0.2100 | 3348 | 0.62 | 16.75 |
| | 3.53 | 1108 | 0.2300 | 3411 | 0.55 | 17.17 |
| | 3.71 | 1170 | 0.2500 | 3453 | 0.60 | 17.48 |
| | 3.88 | 1229 | 0.2600 | 3495 | 0.63 | 17.76 |
| | 4.06 | 1285 | 0.2750 | 3537 | 0.66 | 18.03 |
| | 3.88 | 1290 | 0.2800 | 3497 | 14.27 | 18.06 |
| | 3.71 | 1292 | 0.2850 | 3459 | 14.52 | 18.07 |
| | 3.53 | 1295 | 0.2850 | 3423 | 14.52 | 18.08 |
| | 3.28 | 1300 | 0.2900 | 3375 | 3.69 | 18.11 |
| | 3.28 | 1300 | 0.2900 | 3375 | 3.69 | 18.11 |
| COOLING/ EXIT ZONE | 2.98 | 216 | 0.0178 | 3275 | 20.00 | 18.13 |
| | 2.67 | 216 | 0.0181 | 2476 | 10.07 | 18.15 |
| | 2.37 | 216 | 0.0186 | 1777 | 10.31 | 18.18 |
| | 2.18 | 216 | 0.0192 | 1391 | 3.64 | 18.21 |
| | 1.98 | 216 | 0.0201 | 1047 | 2.27 | 18.28 |
| | 1.79 | 216 | 0.0214 | 748 | 1.72 | 18.37 |
| | 1.60 | 216 | 0.0236 | 498 | 1.45 | 18.49 |
| | 1.41 | 216 | 0.0270 | 300 | 1.37 | 18.63 |
| | 1.22 | 216 | 0.0325 | 159 | 1.49 | 18.76 |
| | 1.03 | 216 | 0.0411 | 72 | 1.93 | 18.87 |
| | 0.83 | 216 | 0.0536 | 28 | 2.87 | 18.95 |
| | 0.64 | 216 | 0.0702 | 7 | 4.49 | 19.01 |
| | 0.45 | 216 | 0.0887 | 0 | 5.82 | 19.04 |

The centrifuge arm 604 length is an important factor as it relates to the pressure within the centrifuge arm 604. The centrifugal forces generated by the centrifuge 200 are related to the distance measured from the center axis 248 of the centrifuge 200 to the particular point within the centrifuge arm ("R" in FIGS. 13–14). The greater the value of R, the greater the pressure in the arm 604. As shown in Table 1 and FIG. 15, the pressure increases from the center of the centrifuge 200 to the end of the centrifuge arm 604 (as the material flows in and through the reaction zone) and then decreases material flows from the end of the centrifuge arm 604 to the center of the centrifuge 200 (as the reaction by-products flow through the center channel 218 or inner tube).

In greater detail, as the sludge slurry is injected into the main body 602 and travels down the influent manifold 644 and into the beginning portion 210 of the centrifuge arms 604, the slurry is not under any appreciable pressure (see Table 1). Both the velocity and temperature of the sludge slurry remain constant in the beginning portion 210 of the centrifuge arm 604. In addition, because the density of the influent remains constant in the beginning portion 210 of the arm 604, the specific volume also remains constant (specific volume is the inverse of density). As the sludge slurry moves from the influent manifold 644 to the middle channel 216 of the centrifuge arm 604, the cross-sectional area of the middle channel 216 begins to decrease as the overall diameter of the middle channel 216 decreases. As the middle channel 216 narrows in diameter, the sludge slurry begins to thicken. This area of the centrifuge arm is known as the sludge thickening zone 202.

In one embodiment, as the sludge thickens, centrate 246 or lighter fluids flow away from the sludge through exit ports in the middle channel 216 into the outer channel 214 and back toward the center of the main body portion 602. The centrate 246 ultimately flows into the effluent manifold 638 and into the discharge chamber 654 in the base of the centrifuge reactor 200. The presence of an outer channel 214 allows the lighter fluid 246, if any, to exit the centrifuge 200 without being part of the oxidation reaction. This lighter fluid 246 is decanted from the sludge by the centrifuge 200 in its normal operation prior to reaching the reaction zone 204. In some circumstances, the influent may not have a high fluid content. In those instances the exit ports and outer channels 214 may not be necessary.

Figure 15:
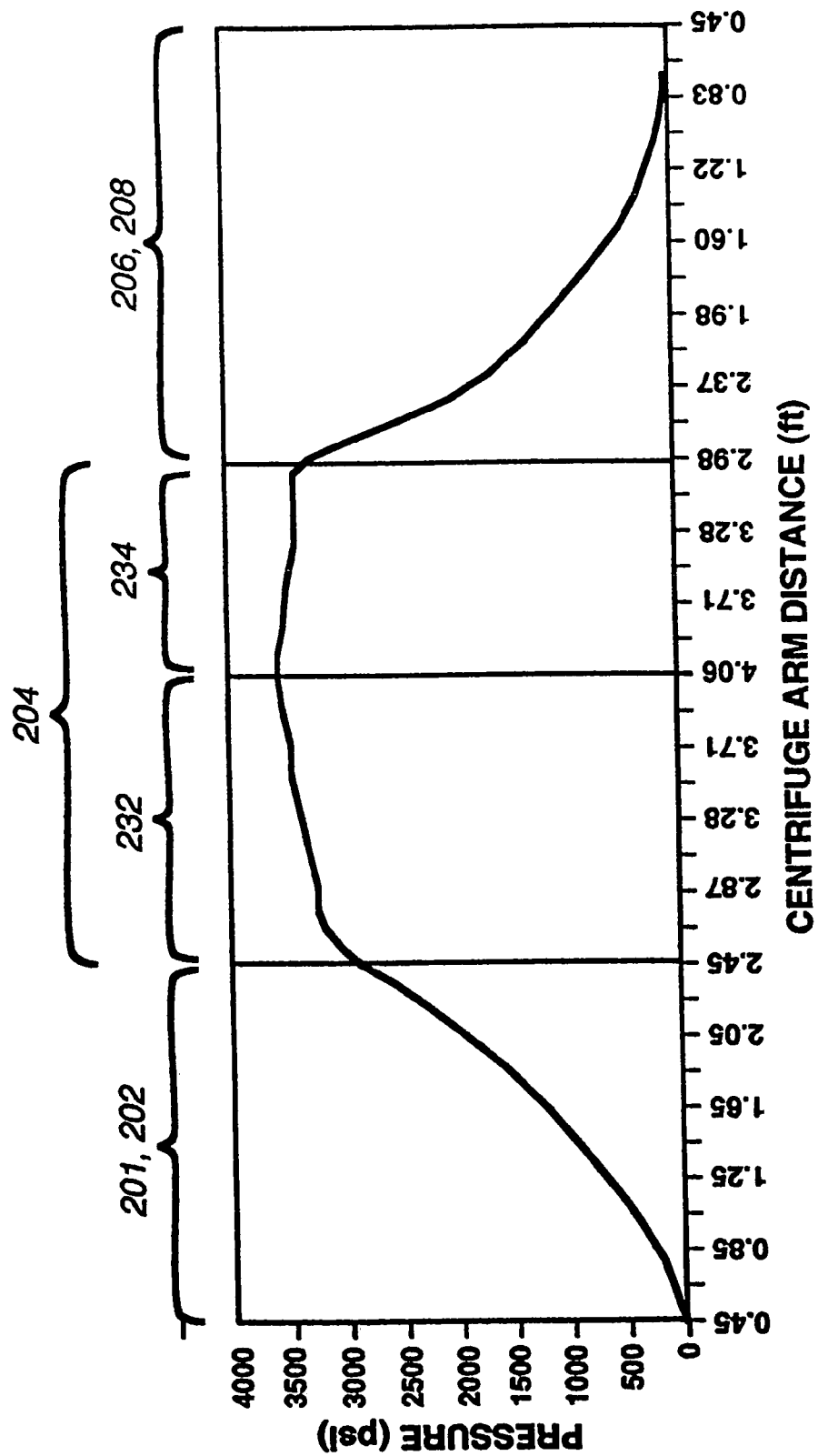
FIG. 15 is a graph illustrating the pressure in the centrifuge arm versus the length of the centrifuge arm.

As illustrated in the graph in FIG. 15 and by the values in column 4 of Table 1, as the influent waste sludge enters the sludge thickening zone 202, the pressure steadily increases. Because the pressure for non-gaseous phase materials is generally P=F/A, where F=force in pounds and A=area in square inches, the decreasing diameter of the middle channel 216 sludge thickening zone 202 causes the cross-sectional area of the middle channel 216 to decrease and thus the pressure to increase. In addition, because the sludge thickening zone 202 forms a partial solids plug in the middle channel 216, the velocity in the sludge thickening zone 202 remains low and constant (see FIG. 17 and column 5 of Table 1). Because the sludge thickening zone 202 is in an area of the centrifuge arm 604 that is not heated, the temperature in the sludge thickening zone remains relatively constant (see FIG. 18 and column 2 of Table 1). The partial plug of sludge helps maintain a relatively constant influent density (and corresponding constant specific volume as illustrated by the graph in FIG. 16 and by the values in column 3 of Table 1) within the sludge thickening zone 202. As the thickened and dewatered sludge exits the sludge thickening zone 202, it is injected with an oxidant, such as oxygen. The dewatered, thickened, and oxidant injected sludge next enters the end portion 212 of the centrifuge arm 604.

The end portion 212 of the centrifuge arm 604 is typically heated using an external heating coil 244. In other embodiments, an electrode internal to the end portion of the centrifuge arm 604 may also be used. The end portion 212 of the centrifuge arm 604 is also known as the oxidation reaction zone 204. The oxidation reaction occurs in this area. The oxidation reaction disintegrates the sludge and creates an effluent mixture of ash, $CO_2$, and $H_2O$. Other by-products may also be present depending on the constituents in the influent material. A combination of high temperatures created by the heating coil 244 and high pressures created by both and the centrifuge 200 and the centrifuge arm 604 geometry act together to create an environment with supercritical conditions. The oxidant enriched sludge undergoes an oxidation reaction in the supercritical environment.

The oxidation reaction zone 204 portion of the centrifuge reactor 200 includes outer 232 and inner 234 chambers. The cross-sectional area of the outer chamber 232 increases and the cross-sectional area of the inner chamber 234 decreases as the influent sludge flows toward the end 212 of the centrifuge arm 604. In the oxidation reaction zone 204, the influent is primarily comprised of materials in the solid and gas phases. As a result, the influent in the oxidation reaction zone 204 responds at least partially according to the ideal gas law (Pv=nRT, where P=pressure, n & R are constants, and T=temperature). If the ideal gas law applies, the pressure and specific volume are directly proportional to the temperature. Regardless of whether the ideal gas law applies, the centrifugal forces generated by the centrifuge 200 cause the pressure to rise steadily as the distance ("R") from the center 248 of the centrifuge 200 increases.

The resulting pressures from the centrifuge 200 and from the increasing temperature in the oxidation reaction zone 204 cause the pressure to increase from the beginning of the outer chamber 232 to the end of the outer chamber 232 in the middle portion of the oxidation reaction zone 204 at the end of the centrifuge arm 604 (see FIG. 15 and column 4 of Table 1). The pressure increases as the sludge flows toward the end 212 of the centrifuge arm 604 and toward the inlet 250 for the inner chamber 234. The inlet 250 for the inner chamber 234 has an area that is significantly smaller than the area of the outer chamber 232 at the end 212 of the centrifuge arm 604. In addition, this point is at the farthest distance from the center axis 248 of the centrifuge 200. As a result, the centrifugal forces and the geometry cause the pressure to increase to a maximum in an area adjacent to the inlet 250 of the inner chamber 234.

The pressure decreases after the sludge flows reverses direction and flows beyond this pinch point 250 and into the inner chamber 234. Although the temperature continues to rise, because substantially all of the influent sludge has been disintegrated in an oxidation reaction in the outer chamber 232, the geometry of the inner chamber 234 begins to have an effect on the pressure of the effluent oxidized sludge mixture. In addition, the centrifugal forces on the effluent sludge decrease as the value of R decreases and the effluent moves closer to the axis of rotation 248. The side section of the inner chamber is generally funnel-shaped 252 and the diameter of the inner chamber 234 includes a constant portion 254 from the end of the centrifuge arm 604 to a portion near the middle of the end portion 212 of the centrifuge arm 604, and a portion 252 with an increasing diameter from the middle 256 of the end portion 212 of the centrifuge arm 604 to the beginning of the centrifuge arm 604 adjacent the main body 602. This increasing diameter helps cause a reduction in pressure (pressure=F/A, F=force in pounds, A=area in square inches, increase in diameter increases cross-sectional area, thus decreasing pressure).

Figure 16:
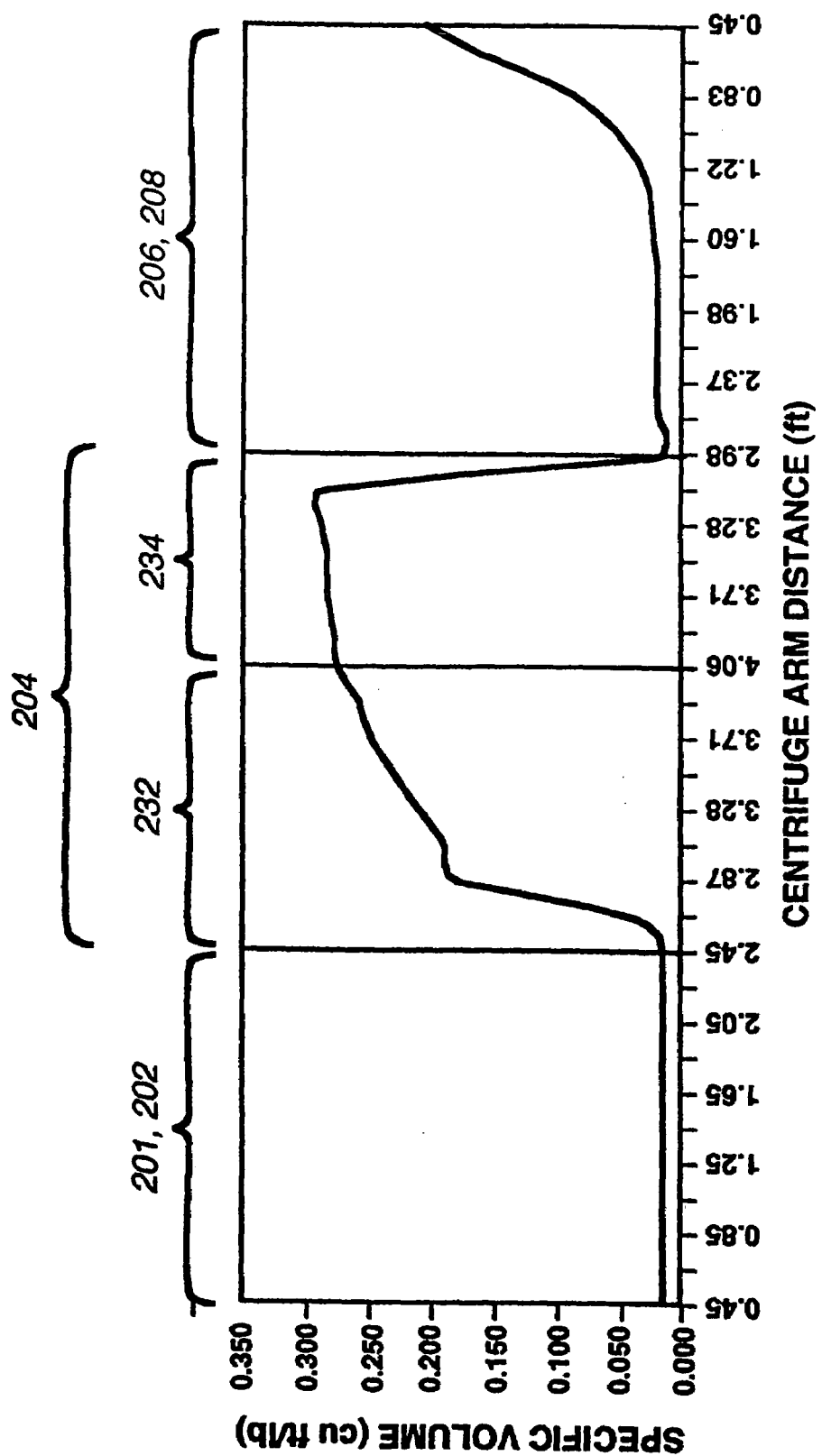
FIG. 16 is a graph illustrating the specific volume in the centrifuge arm versus the length of the centrifuge arm.

The specific volume of both the thickened sludge and oxidized sludge steadily increases throughout the oxidation reaction zone 204 (see FIG. 16 and column 3 of Table 1). As the solids are disintegrated, the density decreases throughout the oxidation reaction zone 204. In addition, because the ideal gas law is assumed to apply in at least the outer chamber 232 of the oxidation reaction zone 204, the fact that the temperature increases causes the volume to increase thereby causing the density to decrease (density=mass/volume). Because density is the inverse of specific volume, the specific volume increases.

Figure 17:
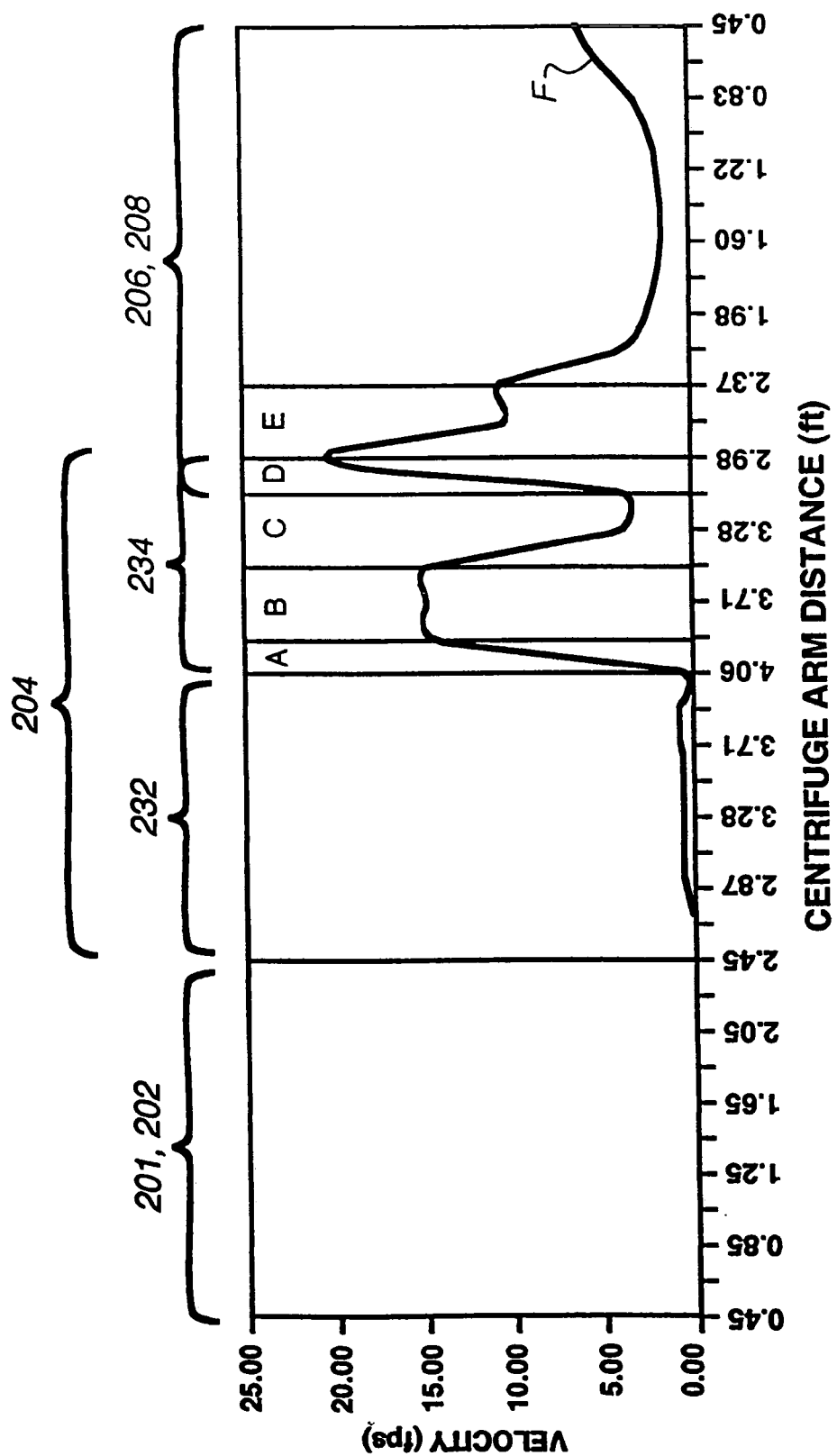
FIG. 17 is a graph illustrating the velocity in the centrifuge arm versus the length of the centrifuge arm.
Figure 18:
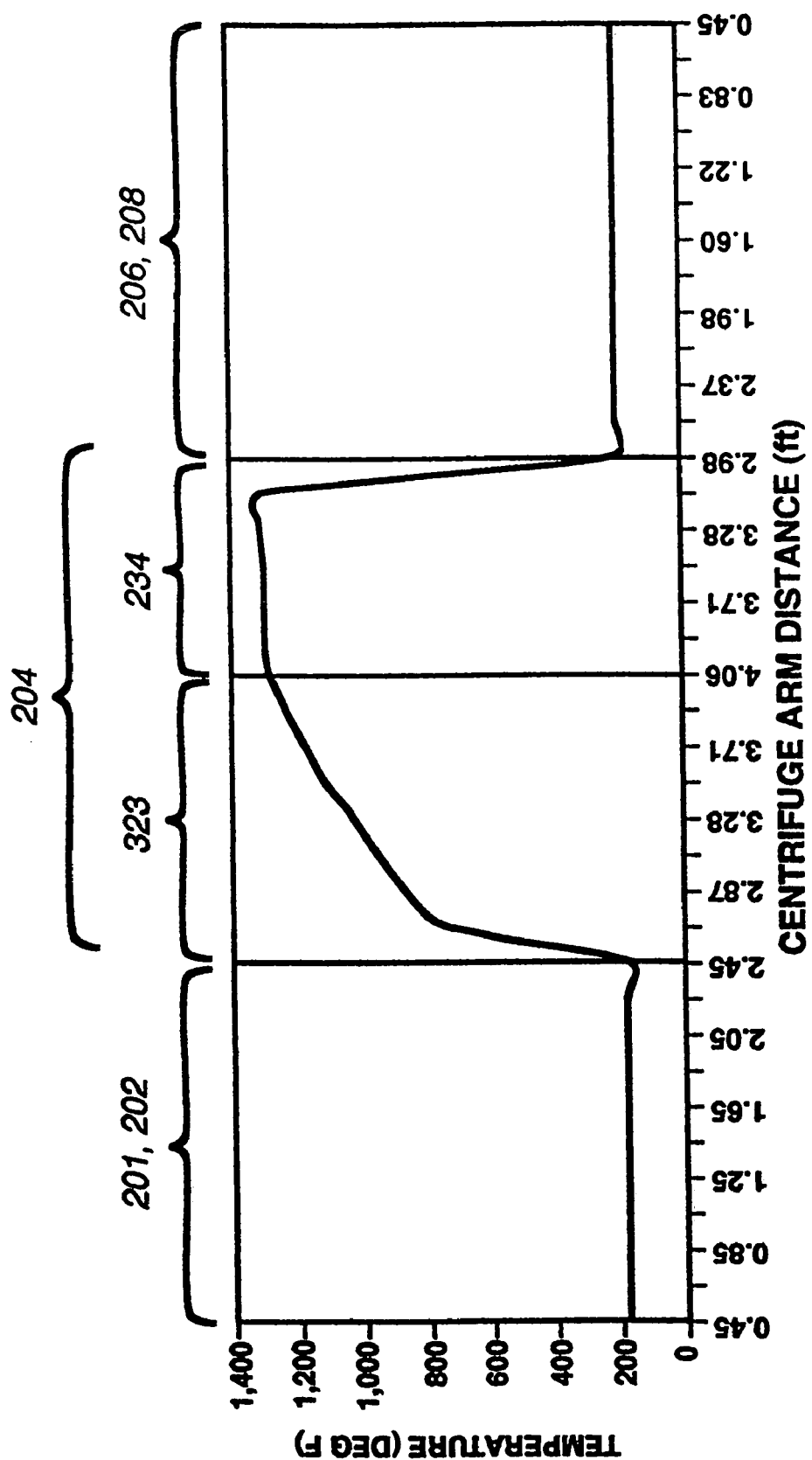
FIG. 18 is a graph illustrating the temperature in the centrifuge arm versus the length of the centrifuge arm.

The velocity of the sludge increases slightly as it moves toward the inlet 250 of the inner chamber 234 (see FIG. 17 and column 5 of Table 1). This increase is a result of the increasing pressure. As the waste moves through the inlet of the inner chamber 234, the velocity of the waste increases dramatically. This increase is due to the effect of moving through the much smaller inlet 250 of the inner chamber 234 (see region "A" of FIG. 17). As the diameter remains constant for the middle third of the inner chamber 234, the velocity also remains constant (see region "B" of FIG. 17). As the diameter of the inner chamber 234 increases, the velocity of the oxidized waste steadily decreases (see region "C" of FIG. 17). Correspondingly, the pressure also decreases steadily as the waste moves from the inlet 250 of the inner chamber 234 toward the larger diameter end 256 of the inner chamber 234. The temperature within the oxidation reaction zone 204 steadily increases as the waste product moves from the beginning 236 of the centrifuge arm to the end 238 of the centrifuge arm through the outer chamber 232 and back to the beginning 240 of the centrifuge arm 604 through the inner chamber 234. The increase in temperature of the waste sludge as it moves through the oxidation reaction zone 204 is primarily a result of the residence time of the waste sludge in the heated zone 204. The longer the waste sludge is heated, the higher the temperature of the waste sludge.

As the oxidized wastes travel further along the inner chamber 234 toward the effluent manifold 638 in the main body 602, the oxidized wastes (effluent) flows around the cooling tube or probe 228 that extends into the inner chamber 234 from the cooling zone 206 center channel 218. The probe 228 introduces cooling water 230 to the ash and $CO_2$ mixture exiting the oxidation reaction zone 204. As a result, the velocity again increases due to the diminished cross-sectional area within the inner chamber 234 (see region "D" in FIG. 17). The resultant effluent of ash, $CO_2$, and $H_2O$ exits the inner chamber 234 of the heated oxidation reaction zone 204 and enters the center channel 218 of the cooling zone 206.

The diameter of the center channel 218 in the cooling zone 206 increases from the beginning of the cooling zone to the end of the cooling zone adjacent the effluent manifold. The geometry of the cooling zone 206 center channel 218 (increasing diameter) causes the pressure in the cooling zone to steadily decrease. The pressure decreases as the effluent moves from the constricted inlet 258 of the center channel 218 to the larger diameter portion of the center channel 218.

As mentioned above, the length of each probe 228 may be adapted to manually or automatically adjust depending on the pressure in each centrifuge arm 604 cooling zone 206. The head 229 of the probe 228 serves as a throttle block 229 to help maintain pressure levels in the reaction zone 204 and to generally help control the entire process. If the probe 228 were substantially removed from the oxidation reaction zone 204 inner chamber 234, the oxidation reactions would discontinue. By substantially removing the probe 228 from the oxidation reaction zone 204, the $CO_2$ gases within the reaction zone 204 are allowed to expand into the cooling zone 206 thereby increasing the volume and decreasing the density. The drop in density correspondingly causes the pressure within the reaction zone 204 to decrease thereby causing the oxidation reaction to discontinue. If the probe 228 is inserted too far into the oxidation reaction zone 204, the cooling water 230 can cause the oxidation reaction to discontinue by quenching the reaction. The cooling water 230 can cause the temperature within the reaction zone 204 to drop low enough to cause the oxidation reactions to cease. The probe 228 can also be adjusted to manipulate the amount of centrate 246 that flows out of the outer channels 214. The further the probe 228 is inserted into the reaction zone 204 (without quenching the reactions), the greater the pressure is within the reaction zone 204. As a result, the pressure in the sludge thickening zone 202 is also increased and the amount of centrate 246 that escapes via the outer channel 214 is increased. If the probe 228 is only inserted far enough into the reaction zone 204 to maintain the oxidation reactions, the pressure levels in the reaction zone 204 will be toward the lower end of acceptable pressure levels to maintain oxidation reactions. As a result, the pressure levels in the sludge thickening zone 202 will also be reduced thereby allowing potentially all of the fluids to pass into the reaction zone 204. In such a case, the centrate 246 flow rate may be greatly reduced or even stopped.

As illustrated best in FIG. 16, the specific volume drops as it enters the cooling zone 206 (in comparison to the reaction zone 204) and then steadily increases throughout the cooling zone 206. The initial drop is the result of a higher density because the $CO_2$ gases are tightly constricted around the probe 228. As mentioned above, the density inversely influences the specific volume. The higher density of the gases creates a lower specific volume. Because the pressure and temperature both decrease in the cooling zone 206, the $CO_2$ gases created from the oxidation reaction begin to expand in the cooling zone 204. As a result, the volume of the effluent expands and the density decreases (density=mass/volume). The specific volume, which is the inverse of density, therefore increases in the cooling zone 206.

The velocity of the effluent increases throughout the cooling zone 206. In the beginning of the cooling zone 206, the center channel 218 cross-sectional area is reduced greatly by the presence of the probe 228 within the channel 218. As a result, the velocity greatly increases through that region (see region "D"). The velocity drops 206 through most of the cooling zone as the cross-sectional area increases (velocity=area/area). At the end of the cooling zone, the expanding $CO_2$ gases cause the velocity to increase as the effluent enters the effluent manifold (see "F" in FIG. 17).

Because of the injection of cooling water 230, the temperature within the cooling zone 206 is significantly less than the temperature in the oxidation reaction zone 204. Also because of the injection of cooling water 230, the temperature within the cooling zone 206 remains substantially constant.

After exiting the cooling zone 206, the cooled effluent mixes with any centrate from the sludge thickening zone and flows into the effluent manifold 638 in the main body 602 portion and down into the discharge chamber 654 at the base of the centrifuge reactor 200. The effluent mixes with cooling water in the discharge chamber 654 to further lower its temperature. As an additional step, the effluent solids may be sent to a filtering process to separate the effluent solids from the effluent fluids.

TABLE 2

Supercritical Wet Oxidation Centrifuge Reactor Parameters

| Parameter | Value | Units |
|---|---|---|
| speed | 2609 | rpm |
| sludge throughput | 50 | gpm |
|  | 417.0 | lb/min |
| influent sludge % solids | 2.0% |  |
|  | 8.3 | lb/min |
| influent sludge temperature | 180 | deg F. |
| influent sludge specific volume | .0165 | cu ft/lb |
| thickened sludge % solids | 16.0% |  |
| thickened sludge throughput | 6.2 | gpm |
|  | 52.1 | lb/min |
| thickened sludge water content | 43.8 | lb/min |
| SHts (specific heat of thickened sludge) | 1.00 | btu/lb/deg F. |
| Sludge % volatile solids | 70.0% |  |
|  | 5.8 | lb/min |
| HVvs (heating value of volatile solids) | 10000 | btu/lb/deg F. |
| $O_2$ dosage requirement | 1.80 | lb/lb VS |
| $O_2$ injected | 10.5 | lb/min |
| $CO_2$ production rate | 2.48 | lb/lb VS |
| $CO_2$ produced | 14.4 | lb/min |
| cooling wet rate | 95 | gpm |
| cooling water temperature | 125 | deg F. |
| $CO_2$ + $H_2O$ produced |  |  |
| in combustion zone | 54.3 | lb/min |
| in cooling zone | 846.6 | lb/min |
| Products % $CO_2$ | 1.7% |  |
| cooling water spec. vol @ | 0.0167 | cu ft/lb |

Table 2 includes parameters for one embodiment of the reactor (also see corresponding FIGS. 13–14). In other embodiments, it is foreseen that the reactor parameters will vary depending on many variables. Examples of such variables include but are not limited to the influent sludge characteristics (i.e., constituents in the sludge), power limitations, and logistical considerations such as the size of the reactor.

In addition to parameters related to the area and the influent characteristics delineated in Table 2, Table 3 includes parameters related to the geometry of the centrifuge arm internal channels and chambers. The location of the various zones in the centrifuge arms with respect to the axis of rotation of the centrifuge is important in relation to the centrifugal forces generated by the centrifuge. Table 3 and FIG. 14 describe and illustrate the various geometrical parameters.

TABLE 3

Supercritical Wet Oxidation Centrifuge Reactor Parameters

| Parameter | Description | Value | Units |
|---|---|---|---|
| R1 | radius from the centrifuge center axis of rotation to the beginning of the heated reaction zone portion of the centrifuge arm | 29.40 | inches |
| R2 | radius from the centrifuge center axis of rotation to the end of the centrifuge arm | 48.70 | inches |
| R3 | radius from the centrifuge center axis of rotation to the middle of the probe head | 39.40 | inches |
| R4 | radius from the centrifuge center axis of rotation to the oxidation reaction effluent ports into the effluent manifold | 5.40 | inches |
| D1 | diameter of centrifuge arm at the end of arm | 6.00 | inches |

TABLE 3-continued

Supercritical Wet Oxidation Centrifuge Reactor Parameters

| Parameter | Description | Value | Units |
|---|---|---|---|
| $r_1$ | radius from the centrifuge center axis of rotation to the centrate exit ports | 0.45 | feet |
| IDmt | inside diameter of oxidation reaction effluent ports | 8.49 | inches |
| $ODit_{min}$ | outside diameter of inner chamber inlet | 1.70 | inches |
| $ODit_{chk}$ | outside diameter of end of inner chamber funnel-like portion | 3.00 | inches |
| $IDit_{min}$ | inside diameter of inner chamber inlet | 1.25 | inches |
| $IDit_{chk}$ | inside diameter of end of inner chamber funnel-like portion | 2.50 | inches |
| $IDit_{max}$ | maximum inside diameter of center channel (inner tube) | 7.00 | inches |
| ODct | outside diameter of probe or cooling tube | 2.00 | inches |
| X1 | length of sludge thickening zone | 1.00 | inches |
| X2 | length of funnel-like portion of inner chamber | 3.00 | inches |
| X3 | length from sludge thickening zone to wide end of funnel-like portion of inner chamber | 11.00 | inches |
| Vchk | velocity of effluent adjacent probe throttle block | 20.0 | feet/second |
| Amax | maximum cross-sectional area of reaction zone | 26.00 | $inches^2$ |
| Amin | minimum cross-sectional area of reaction zone | 21.21 | $inches^2$ |
| $Ait_{min}$ | minimum cross-sectional area of inlet of inner chamber | 1.23 | $inches^2$ |
| $Ait_{chk}$ | maximum cross-sectional area of inner chamber adjacent wide end of funnel-like portion | 4.91 | $inches^2$ |
| $Ait_{max}$ | maximum cross-sectional area of inlet of inner chamber | 38.48 | $inches^2$ |

Figure 19:
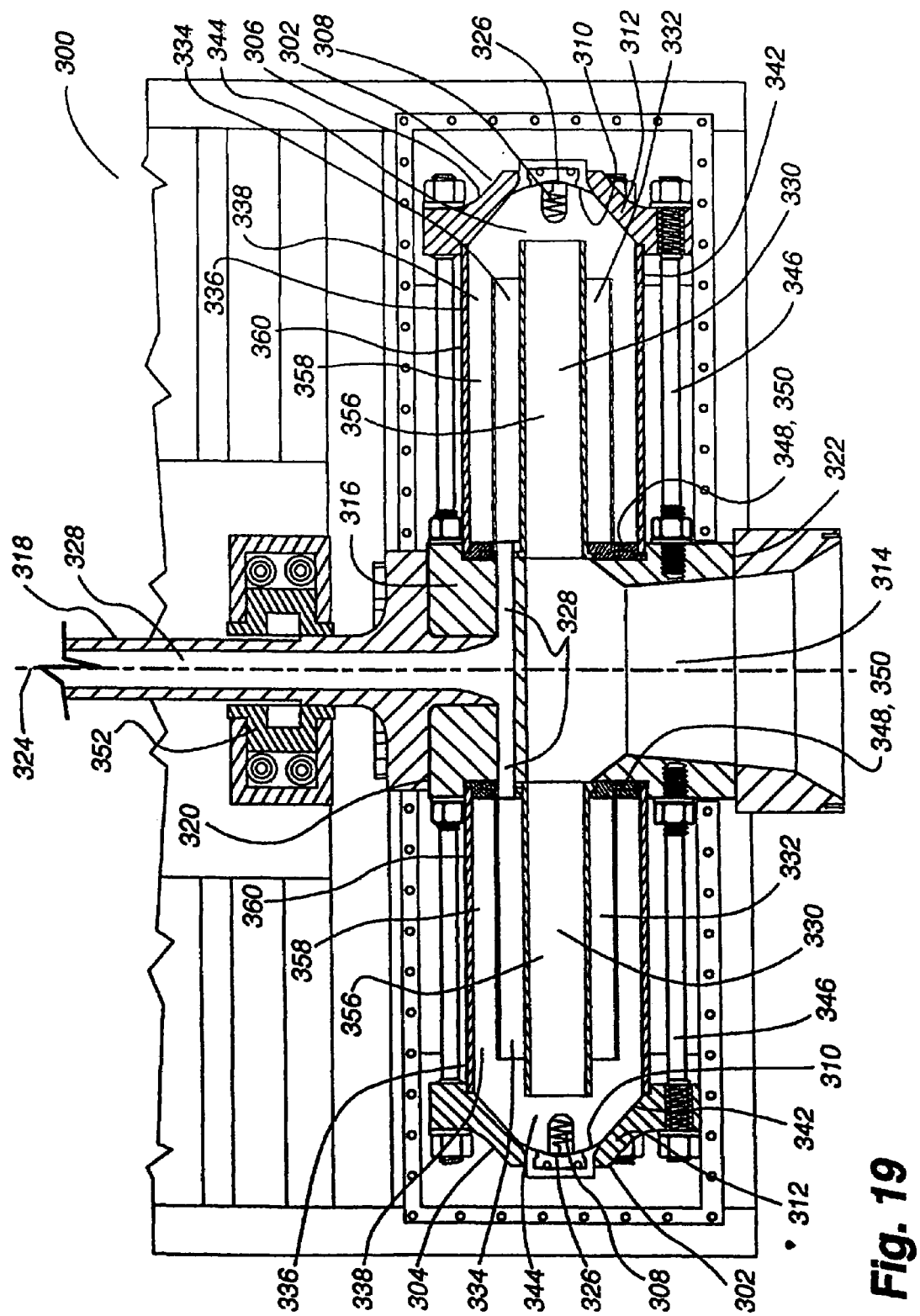
FIG. 19 is a representative section of a centrifuge of the present invention configured for use as an oxidation reactor, including a heat source positioned at the distal end of both arms.

Referring first to FIG. 19, the basic centrifuge structure as described above is slightly modified to structurally convert the centrifuge from traditional applications to a structure suitable for use as an oxidation reactor. Hereinafter, mention is made of the centrifuge as being used in a supercritical oxidation reaction process. It is contemplated that the centrifuge can also be used in a subcritical oxidation reaction process as well as in basic chemical reaction processes. For convenience, the term "oxidation reaction process" is used as a nonlimiting descriptive term.

Referring first to FIG. 19, a section view of a centrifuge 300 modified for use as an oxidation reactor is shown. The basic structure of this centrifuge is identical to that described above, with similar parts given similar descriptive labels. However, similar parts are given different numbers in the descriptions of the various embodiments herein. For example, in one embodiment the main body of the centrifuge may be numbered 316 while in another embodiment, the main body is 402. The primary distinction between FIG. 19 and an earlier described embodiment of this invention is that the structure has been modified to include a heat source 326 at the terminal end 302 of each of the arms 304, 306. In this instance, an electrode 308 is provided attached to the inner side 310 of the end cap 312. Any type of heat source 326 can be used which is sufficient to raise the internal temperature in the reaction zone defined at the end of each of the arms 304, 306 to the critical temperatures. Such heat sources 326 include, but is not limited to, glow plugs, electric resistive heaters, and radiative heaters. An additional change is that the augers used to remove the heavy material from the centrifuge structure as described above have been themselves removed to allow exit of the reacted by-products, or reactants, through the outlet aperture 314, as described below.

The structure of FIG. 19 includes a main body 316 with at least two diametrically opposed arms 304, 306 extending therefrom. An inlet pipe 318 connects to one end 320 of the main body 316, and an outlet aperture 314 is formed on the opposite end 322 of the main body 316. The inlet pipe 318 carries material to the main body 316, and also forms the axis 324 about which the centrifuge 300 rotates. Typically, the centrifuge 300 spins on a vertical plane (into and out of the page in FIG. 19) but can be oriented in any manner desired. Various channels are formed inside the main body 316 and arms 304, 306 of the centrifuge 300, as described above and below herein.

An inflow channel 328 is formed by the inlet pipe 318 and extends from the inlet pipe 318 into both of the arms 304, 306. The inflow channels 328 in both arms are identical, so only the flow channels 328 in one arm are described herein. Inside the arm 304 there is a central tube 330 that acts as an exit path and is in communication with the outlet aperture of the main body 316. Spaced concentrically outwardly from the central tube 330 and attached to the main body 316 is an intermediate tube 332, which forms an annular space around the central tube 330. This inner annular space 334 is part of the inflow channel 328 incoming flow path for the incoming sludge material. The arm housing 336 forms an annular space 338 around the intermediate tube 332. This outer annular space 338 forms part of the exit path for the decanted liquids as described above. The outer annular space 338 is in communication with the high fluid (decanted liquid) exit channel 340 formed in the main body as described above. The central tube 330 can be somewhat longer than the intermediate tube 332 for reasons described above.

The end 342 of the arm 304 forms a cavity 344, which is the reaction zone for the oxidation reactor. The curved cavity 344 is defined by an end cap 312, which is held in place by a series of elongated bolts 346, which extend from the end cap 312 to the main body 316. Each tube has its own base frame 348 which fits into the main body 316 and interlocks with the base ring 350 of the adjacent tube, and under the compressive force of the attachment bolts 346, each of the base rings 350 form a tight seal with the main body 316, as described above. The interlocked base rings 350 allow the sectional formation and removal of the arm 304 and its inner parts. The end cap 312 seats on the outer end 342 of the arm housing 336 and under the compression of the elongated bolts 346, compressing the arm housing 336 towards the main body 316. The base ring 350 of the arm housing 336 interlocks with the base ring 350 of the intermediate tube 332, which in turns interlocks with the base ring 350 of the inner tube 330, and thus holds all of the tubes in sealed engagement with the main body 316.

A set of bearings 352, only one of which is shown, supports the inlet pipe 318, and thus also the cantilevered centrifuge 300. As the centrifuge 300 spins, preferably with the arms 304, 306 moving in a vertical plane, great pressures are formed at the ends 342 and each arm 304, 305 in the reaction zone area. The pressure is determined primarily by the revolutions per minute (spin speed) and the length of the arm 304, and is easily controlled. As noted above, a motor (not shown) is used to spin the centrifuge 300, preferably by turning the inlet pipe 318.

A heating element 326, such as an electrode 308, is positioned in the reaction zone to provide the heat required for the supercritical oxidation reaction process. The temperature required for the oxidation reaction to occur is described above in detail, and is generally above 700° F. and 3200 psi.

Oxygen is required, along with heat and pressure, to cause the oxidation reaction to occur. Oxygen can be fed directly into the reaction zone by a separate piping system (not shown in this embodiment) or can be permeated in the incoming sludge material as it enters the centrifuge 300. In either manner, oxygen is brought into the reaction zone in addition to the heat and pressure in the reaction zone, helping facilitate the oxidation reaction taking place.

Generally, when the sludge plug forms in the reaction zone, and the sludge is subjected to extreme pressures, heat, energy and oxygen, the oxidation reaction process occurs. The by-products of the reaction oxidation process are typically mainly ash, $CO_2$ or $H_2O$. The reaction by-products can also include other elements which are not entirely transformed during the reaction process to ash, $CO_2$ or $H_2O$, depending upon the constituents of the incoming sludge. The reaction by-products exit the centrifuge through the inner tube 330, as is described in more detail below. Because the reaction zone is at very high pressure and the exit aperture 314 is at ambient pressure, the reaction products will somewhat automatically flow through the inner tube 330 toward the outlet aperture 314 due to the pressure drop. As the reaction products flow through the inner tube 330, at some intermediate position 356 of the inner tube 330, there is a flash steam zone where the pressure has decreased sufficiently to allow the $H_2O$ reaction by products to transition to a steam state. This further helps expel the reaction by products out the outlet aperture 314, which is a atmospheric pressure.

In more detail, in the instant invention, with respect to FIG. 19, the incoming sludge preferably includes a sufficient oxidant level to withstand being compacted as it moves from the inlet 318 to the end of the arm 342, as described above. The decanted liquid is extracted to dewater the sludge prior to the oxidation reaction. The sludge concentrates as it moves to the reaction zone at the distal end 342 of the arm 304. With the addition of heat and with the oxidant in the compacted material, the oxidation reaction process occurs in a reaction zone. The oxidation reaction is started by the heat energy in combination with the oxidant and the fuel content of the material. Once it begins, the oxidation reaction is preferably self-sustaining and the heat source can be turned off. It can be turned on as needed to maintain the desired temperature. The resulting reaction by-products are flushed from the centrifuge 300 through the inner tube 330 and out the outlet aperture 314. The removal of the decanted liquid is identical to that described above.

Generally, a temperature of approximately 800 to 1200 degrees Fahrenheit is required for the oxidation process to occur. The pressure generated at the end 342 of the centrifuge arm 304 in the reaction zone should be approximately 3,000 to 3,500 psi, and the required oxidant level depends on the volatility of the material in the mixture being oxidized in the reaction. While the oxidant can be included in the incoming material, it is more efficient if it is added to the heavier material as it is compacted. The compaction (drying out) process removes some of the oxidant from the material. If the oxidant is added after the majority of the compaction has occurred, then only the necessary level of oxidant is required to be added to the material. These values are representative only, as are the values described elsewhere herein.

In using the centrifuge 300 of the present invention as an oxidation reactor, the pressure can be easily controlled by the length of the arm 304 extending from the main body 316 and the spin speed of the centrifuge 300 itself. This is a significant advantage over the existing supercritical oxidation reactor processes which require complex pressure generation, release and control equipment. Further advantages are described hereinafter. The reaction products from this process can be taken directly from the outlet aperture 314 and disposed of as desired, such as being encased in concrete or handled by any other known type of disposal techniques.

It is contemplated that the centrifuge 300 of the present invention can be connected in series with at least a second centrifuge, if desired. For instance, a first centrifuge can be used to de-water the sludge to a sufficient level for the oxidation reaction process, with the outlet of the first centrifuge being connected to the inlet of the second centrifuge. If the second centrifuge is modified to act as an oxidation reactor, then the outlet of the first centrifuge can flow into the inlet of the second centrifuge where the oxidation reaction process takes place. Several centrifuges can also be hooked together if desired.

During the oxidation reaction process, whether critical, subcritical, supercritical, or any other reaction process performed in the centrifuge 300 of the present invention, the process parameters can be monitored and controlled by the placement of appropriate sensors in the centrifuge 300, combined with automatic feedback of the sensor data to either a human-controlled center, or to an automated center including a computer, microprocessor, and the desired programming software to interpret and respond to the feedback from the sensors. The sensors can be placed in several places in the centrifuge 300 for monitoring the critical process characteristics, such as along the inside 358 or outside 360 of the arm 304, in the reaction zone, in the exit tube 330 and outlet aperture 314 areas, and in the inlet path 328 as well as the inlet pipe 318. The sensors allow the measurement of the physical characteristics such as, but not limited to, the heat level, the oxidant content and the pressure. The control system, whether human or automated, can react to the sensor data to decrease, increase or maintain the various input data, such as spin speed, temperature, oxidant content and possibly even sludge chemical makeup to help optimize the oxidation reaction.

The centrifuge 300 of the present invention used as an oxidation reactor is not limited to two diametrically opposed arms 304, 306. It is contemplated that any number of arms can be implemented as long as the proper balance is created to allow the spin speeds required to generate the desired pressure.

Figure 25:
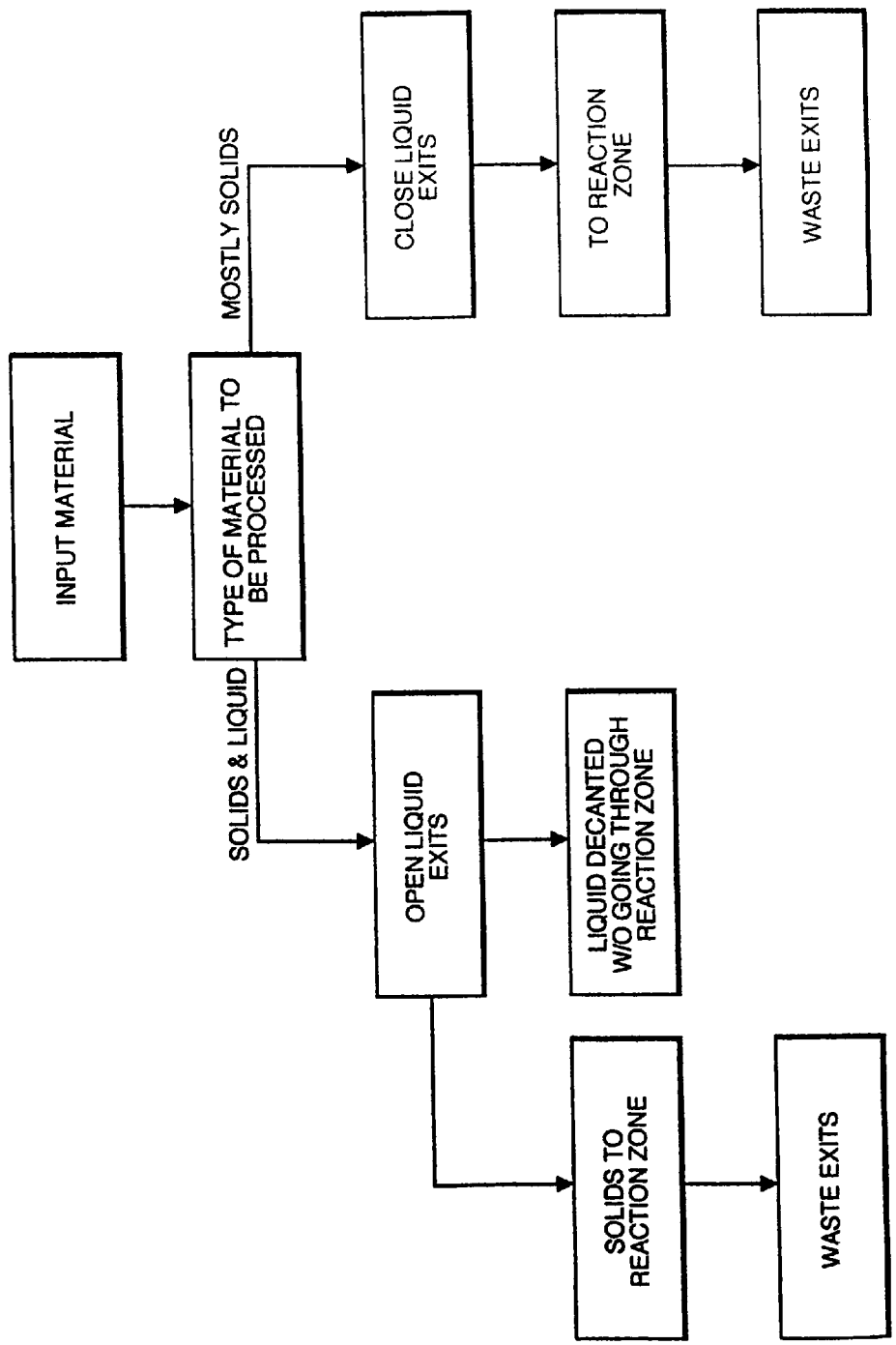
FIG. 25 is a flow chart representing the process related to selecting whether or not the oxidation reactor should include an exit flow path for a centrate.

It is also contemplated that the outlet flow path 334 for the decanted liquid can be blocked to make all of the input sludge material in the inlet pipe 318 go through the reaction zone in a case requiring the entire content of the sludge to be reacted. The decanted liquid outlet apertures (not shown) can be permanently covered up or selectively covered up so that the same reactor can decant the liquid to force mainly solids through the oxidation reaction process, or can force both liquids or solids (preferably in a slurry form) through the reaction zone. Each has its benefits for different kinds of sludge material, and can be selected as desired. FIG. 25 is a flow chart of the basic steps involved in the process of closing or keeping open the liquid exits 366.

Another benefit of the current invention is that the inlet sludge is subject to a gradually increasing pressure gradient when entering the reaction zone, and a decreasing pressure gradient when exiting from the reaction zone to ambient pressure through the outlet aperture 314. The pressure drop from the reaction zone to ambient pressure in the outlet aperture 314 facilitates in flushing the reaction products through the center tube 330 and out of the centrifuge 300.

Figure 20:
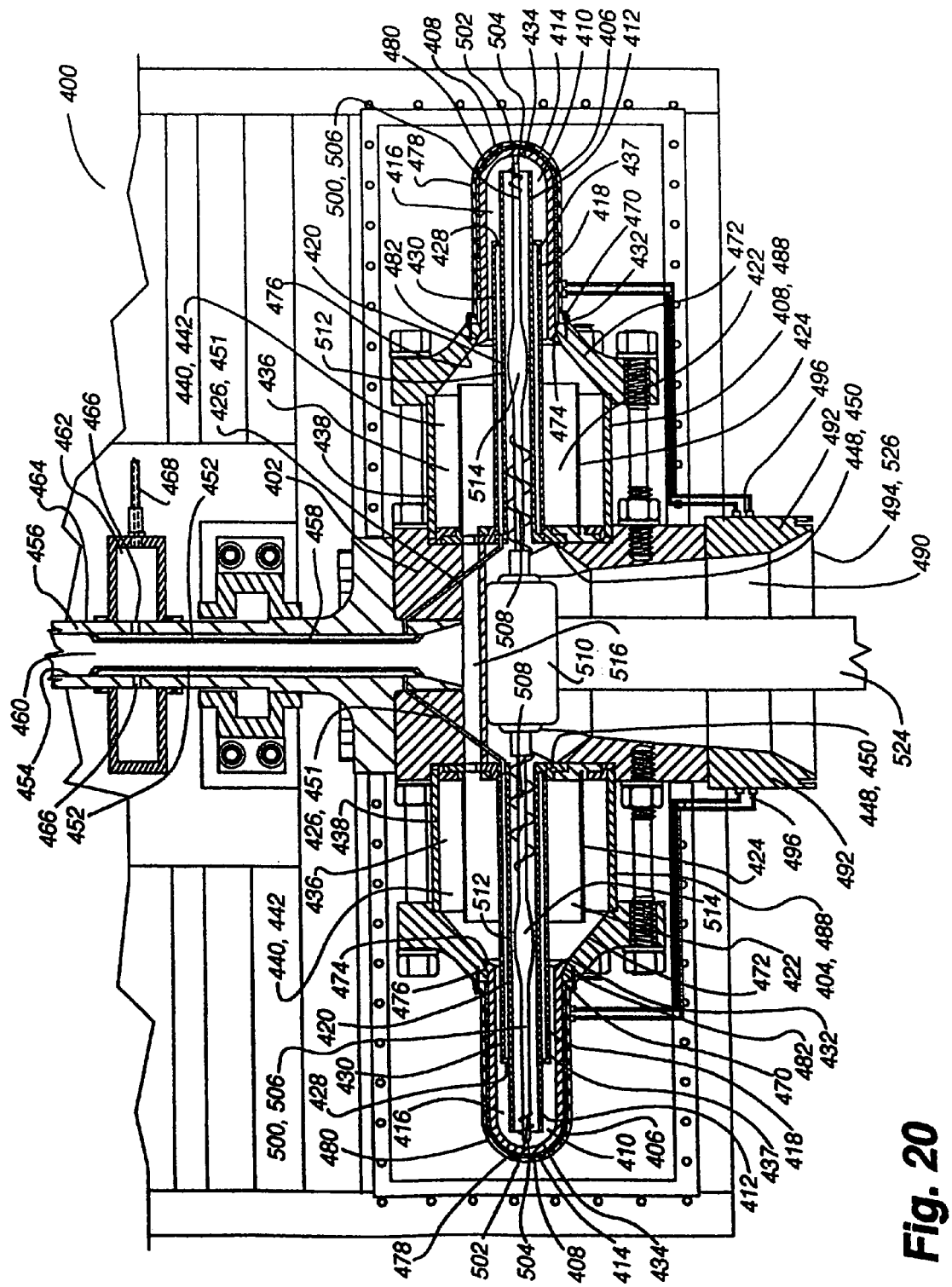
FIG. 20 is a representative section of another embodiment of the present invention configured for use as an oxidation reactor.

FIG. 20 shows another embodiment of the centrifuge structure 400 as modified for use as an oxidation reactor. Primarily, the main body structure 402 and arm structure 404 are identical to the previous embodiment described above (although the arms 404 are relatively shorter than in the previous embodiment). The primary distinction is that the end caps are replaced with elongated tubes 406 having rounded ends 408 to create a longer reaction chamber region 410. In this embodiment, the inner tube 412 extends to a position adjacent the outer end 414 of the elongated end cap tube 406, and is inside the reaction chamber 416. A sheath 418 is formed about the inner tube 412 and extends to approximately one-half or three-quarters the length of the inner tube 412 and terminates about the mid-point of the end cap tube 406. An inner annular space 422 is also formed between the intermediate tube 424 and the sheath 418, which forms a part of the sludge input path 446. The sheath 418 forms an annular space 420 around the inner tube 412, the annular space 420 being very small compared to the annular space 422 formed between the intermediate tube 424 and the inner tube 412 (or sheath 418). The annular space 420 formed around the inner tube 412 by the sheath 418 is part of the oxidant inlet flow path 426 for the addition of oxidant to the inlet sludge material. The distal end 428 of the sheath 418 is perforated on its perimeter 430 to allow the oxidant to mix with the inlet sludge as it passes by the sheath 418 as it moves along the inner tube 412 towards the reaction zone. A small annular space 437 is defined around the inner tube 412 and sheath 418 by the end tube 406 as they extend into the end tube 406. The intermediate tube 424 extends approximately one-half the length of the inner tube 412 and terminates near the end of the arm 432, well away from the end 434 of the reaction chamber 416. An outer tube 436 is formed by the arm housing 438. An outer annular space 440 is formed between the outer tube 436 and the intermediate tube 424 and defines a decanted liquid exit path 442.

The oxidant inlet path 426 extends from the base 448 of an annular region 450 formed by the sheath 418, through a channel 451 in the main body 402, and is connected to an outer annular space 452 formed on the inside 454 of an inlet pipe 456. This outer annular space 452 is formed by a tube 458 welded or connected inside the inlet path 460 to the inner walls 454 of the inlet pipe 456. The outer annular space 452 in the inlet pipe 456 is in fluid connection with an oxygen manifold 462 rotatably mounted on the exterior 464 of the inlet pipe 456. The manifold 462 is attached to an oxidant source, such as a tank or oxidant line 468. The oxidant thus flows into the oxidant manifold 462, through the apertures 466 formed on the wall 454 of the inlet pipe 456, and into the outer annular region 452 of the inlet pipe 456. The oxidant flows along the inlet pipe 456 in the outer annular region 452 to the oxidant channel 451 flowing through the central body 402 of the centrifuge 400 to the base 448 of the annular region 450 formed between the sheath 418 and the inner tube 412. The oxidant then flows along the length of the inner tube 412 to the perforated holes 430, where it then mixes with the incoming sludge to add oxidant the sludge and prepare it for the oxidation reaction.

The arms 404 of the tubes are shorter in this embodiment than in the previous embodiments described to allow for the elongated end cap tube 406, with the total centrifuge 400 diameter remaining approximately the same. The arms 404 could be longer or shorter as desired and the end tubes 406 could be longer or shorter as desired to define the proper external dimensions of the centrifuge 400 as well as the proper size of reaction chamber 416. Currently, as described herein, the reaction chamber 416 or zone is approximately one-quarter to one-half of the total length of the arm 404 of the centrifuge 400.

The tubular end cap 406 is formed of a material, such as metal, that is sufficiently strong and resilient enough to withstand the high pressure and temperature of the oxidation reaction occurring with the end cap 406. The tubular end caps 406 are effectively bell-jar shaped with an internal flange 470 that wedges against the semi-conical, frusti-conical end cap collar 472. The centrifugal force from spinning causes a positive engagement between the angular flange 470 around the bottom 474 of the tubular end cap 406 and the inner wall 476 of the semi-conical end cap collar 472.

A heating element 478 is positioned around the tubular end cap 406, preferably around its entirety, about which an insulated layer 480 is positioned and held in place by fasteners 482 attaching to the end cap collar 472. The heat source 478, as noted above, can be any suitable heating element. The heat source 478 can be inside the arm 404 and end cap 406 or outside the arm 404 and end cap 406, and can cover all of or part of the arm 404 and end cap 406 surrounding the reaction zone. For instance, the heat source 478 could be a band formed around the circumference of the arm 404 or end cap 406, or can be a stripe extending longitudinally along the arm 404 or end cap 406. The heat source 478 is preferably covered by an insulating material to assist in energy efficiency. As noted above, the heat source 478 can be turned off or otherwise controlled as needed after the oxidation reaction has begun.

Oxidant is added to the sludge through the oxidant source that flows from the annulus 462 surrounding the inlet pipe 456 to the pathway 450 through the central body 402, which in turn leads to the sheath 418, which forms the annular space 420 around the inner tube 412. A length of the sheath 418 near its distal end 428 is perforated 430 to allow the oxidant to permeate the sludge that passes over the sheath 418 as the sludge flows towards the end 434 of the reaction chamber 416 to form the plug. The sheath 418 is preferably perforated 430 around its circumference for the oxidant to be evenly dispersed into the sludge. The amount of oxidant dispersed into the sludge depends on the pressure of the oxidant in the in-feed line 468 and the compaction level of the dewatered sludge. The level of oxidant to be diffused into the sludge depends on which type of sludge is to be incinerated in the oxidation reaction process. The oxidant is preferably diffused into and around the sludge after it is de-watered substantially in order to efficiently use the oxidant. If added prior to the compaction step, some of the oxidant is lost in the compaction process.

The oxidant can be inserted through injectors (not shown) placed through the wall 488 of the housing 438 at the desired location. These injectors can be positioned as desired and needed, and can be replaced, removed and maintained. The injectors are fed oxidant by a different source path than that described above for the sheath 418, such as by individual lines running to each injector. Other oxidant insertion means can be used also.

Figure 21:
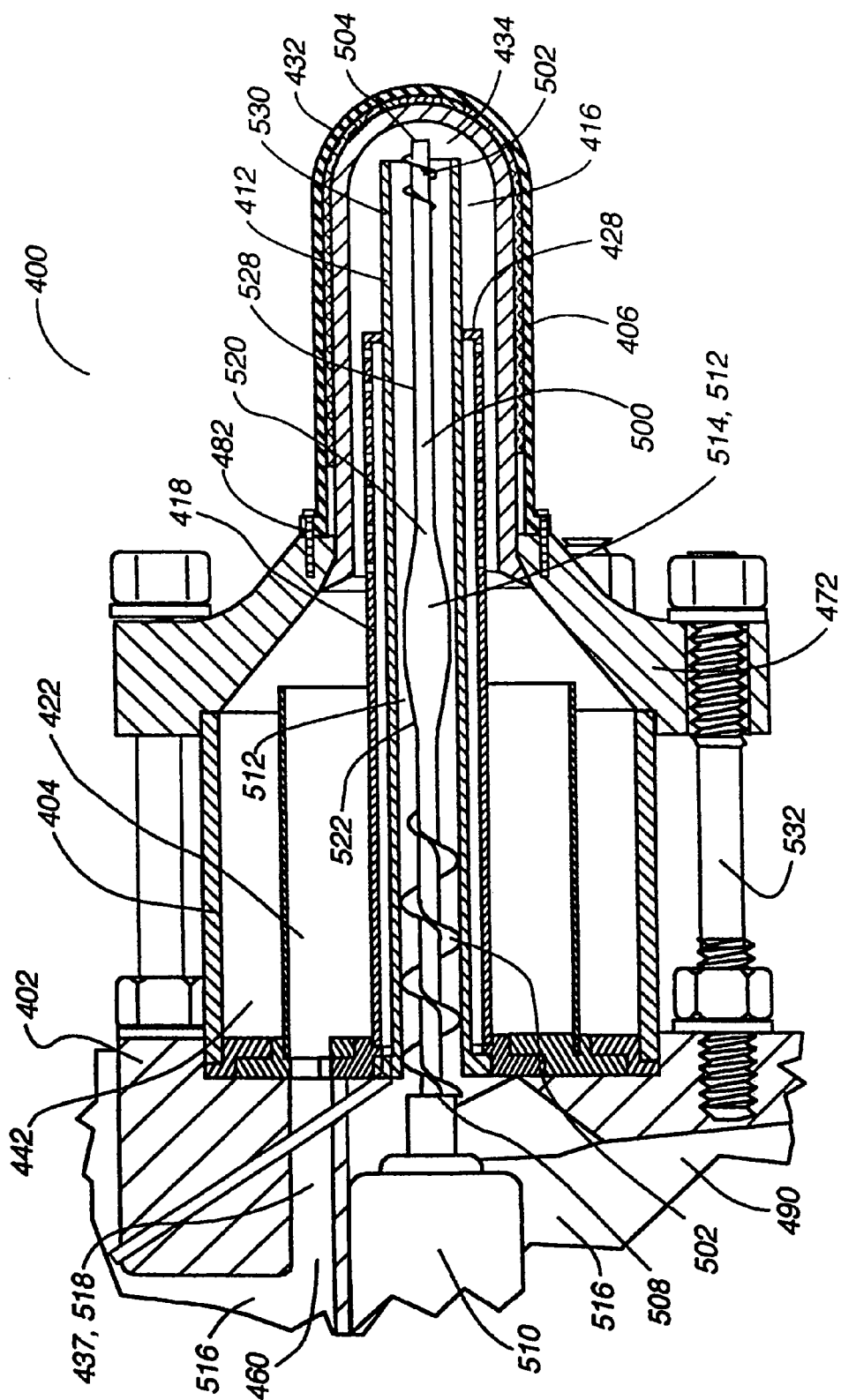
FIG. 21 is an enlarged view of one of the arm sections of the oxidation reactor shown in FIG. 20.

In FIGS. 20 and 21, the heat energy required for the oxidation reaction is generated by a heating element 478 positioned around the entirety of the external side of the reactor and tubular end cap 406. The tubular end cap 406 is preferably made of metal to conduct the heat efficiently. The heating element 478 in the instant case is an electrical coil, but could also be any other adequate means to provide the required temperature level, such as but limited to, a radiation or other source of heat energy for this application. The electric heating element 478 is supplied with electricity by contacts, such as brush contacts 496, that engage an electrically charged collar 492 near the outlet aperture 490 of the centrifuge 400. The collar 492 at the bottom 494 of the main body 402 is rotationally attached to the bottom 494 of the main body 402 and stays stationary with respect to the main body 402 as the main body 402 rotates. The brushes 496 contact the collar 492 and the brushes 496 rotate therearound with the centrifuge 400, to provide electrical connection for supplying energy to the heating elements 478. Any other manner of providing the required energy for actuation of the particular type of heating element 478 used is acceptable. As one alternative example, electromagnetic induction coils could be used (placed circumferentially around the rim) so that when the centrifuge is spun through a magnetic field the coils heat up, as is known in the art. The magnetic field is then able to be turned on, off, or adjusted to control the heat applied to the reaction zone. As mentioned above, an insulating cover (not shown) surrounds the heating element 478 to make the heating element 478 more efficient.

In this embodiment, an auger/choke arm 500 is positioned inside each of the inner tubes 412. The arm 500 is similar to the augers described above with flighting 502 positioned at its distal end 504 to help draw material into the center 506 of the inner tube 412, and flighting 502 attached near the proximate end 508 of the arm 500 where the arm 500 attaches to the central hydraulic motor 510. The positioning of this flighting 502 can be varied depending on the particular oxidation reaction and the requisite desired output characteristics. At a mid-portion 512 of the arm 500, a choke 514 is formed which is an enlarged region 514 of the arm 500, which takes up a majority of the space within the inner tube 412.

FIG. 21 shows one side of the centrifuge 400 represented in FIG. 20. The raw sludge or raw material flows into the centrifuge 400 through the entrance path 460 and then into the arm 404. If the liquids are desired to be decanted, the liquid exit paths 442 are kept open and the decanted liquids flow back toward the center 516 as shown in FIG. 21 to exit the centrifuge 400 as described above. The solids, which are somewhat de-watered, move towards the end of the arm 432. The solids are compacted as they flow into the small annular space 437 defined around the inner tube 412 and sheath 418 as they extend into the end tube 406. This pinch point 518 helps de-water the sludge. The oxidant is preferably introduced at, near or after this point 518. The sludge forms a plug at the end 434 of the reaction chamber 416. As they move down the arm, they pass along the sheath 418 and begin compaction. As the compacted solids move along the sheath 418 over the perforations, the oxidant is dissolved into the solids and otherwise introduced into the reaction zone at the desired level for maintaining the oxidation reaction process.

The de-watered sludge then passes beyond the end 428 of the sheath 418 and contacts the inner tube 412 at which point it flows to the end 434 of the reaction chamber 416 in its de-watered, concentrated condition. At this location in the reaction chamber 416, the temperature, pressure and oxygen content are all established to support the oxidation reaction process.

As described above, after the oxidation reaction occurs, the by-products of the oxidation reaction process are initially augured out by the central auger 500 down the inner tube 412 towards the main body 402 of the centrifuge 400. The flighting 502 at the distal end 504 of the auger 500 helps the reaction by-products begin the path towards exiting the centrifuge 400. Flighting 502 at the proximate end 508 of the auger 500 helps push the waste products out the exit aperture 490.

The choke 514 formed along the central part 512 of the auger 500 controls the pressure of the reaction chamber 416, that is, it maintains the pressure in the reaction chamber 416 to control the flash of the pressurized water to steam as it exits past the choke 514. The choke 514 is mainly an enlarged portion 512 of the auger 500 that consumes the volume of the space inside the inner tube 412. The volume of the choke 514 depends on the amount of control of the flashpoint of the pressurized water to steam as is desired. The choke 514 can take many forms, such as that shown, being an area of increased diameter with gradual front 520 and rear 522 edges, or it can be an area of increased diameter with abrupt front and rear edges, such as a disk mounted transversely inside the inner tube 412. The shape and position of the choke 514 depends on the pressure to be controlled and the physical characteristics of the "flash to steam" process. The choke 514 can have grooves formed longitudinally therein, or other such features, as an additional manner to help control the pressure on either side of the choke 514.

The augers 500 are driven in the inner tube 412 by the hydraulic motor 510 positioned in the center 516 of the main body 402, as is described above. The auger 500 is driven by a hydraulic motor 510, which drives the auger 500 at a selected speed independent of the spin speed of the centrifuge 400. The hydraulic motor 510 is driven by pressurized hydraulic fluid and is fed by a separate shaft 524 inserted into the main body 402 from the end 526 opposite the inlet channel 460.

The heat transfer from the inner annular space 422 to the inside 528 of the inner tube 412 is (through the wall 530 of the inner tube 412 or the combination of the sheath 418 and the inner tube 412) is preferably minimized. The sheath 418, if used, helps provide an insulating layer. Otherwise some sort of insulation is used on the inner tube walls 530.

As in the embodiment described above, the end cap collar 472 is held in place by bolts 532 that when tightened pull the entire arm 404 towards the main body 402.

Figure 24:
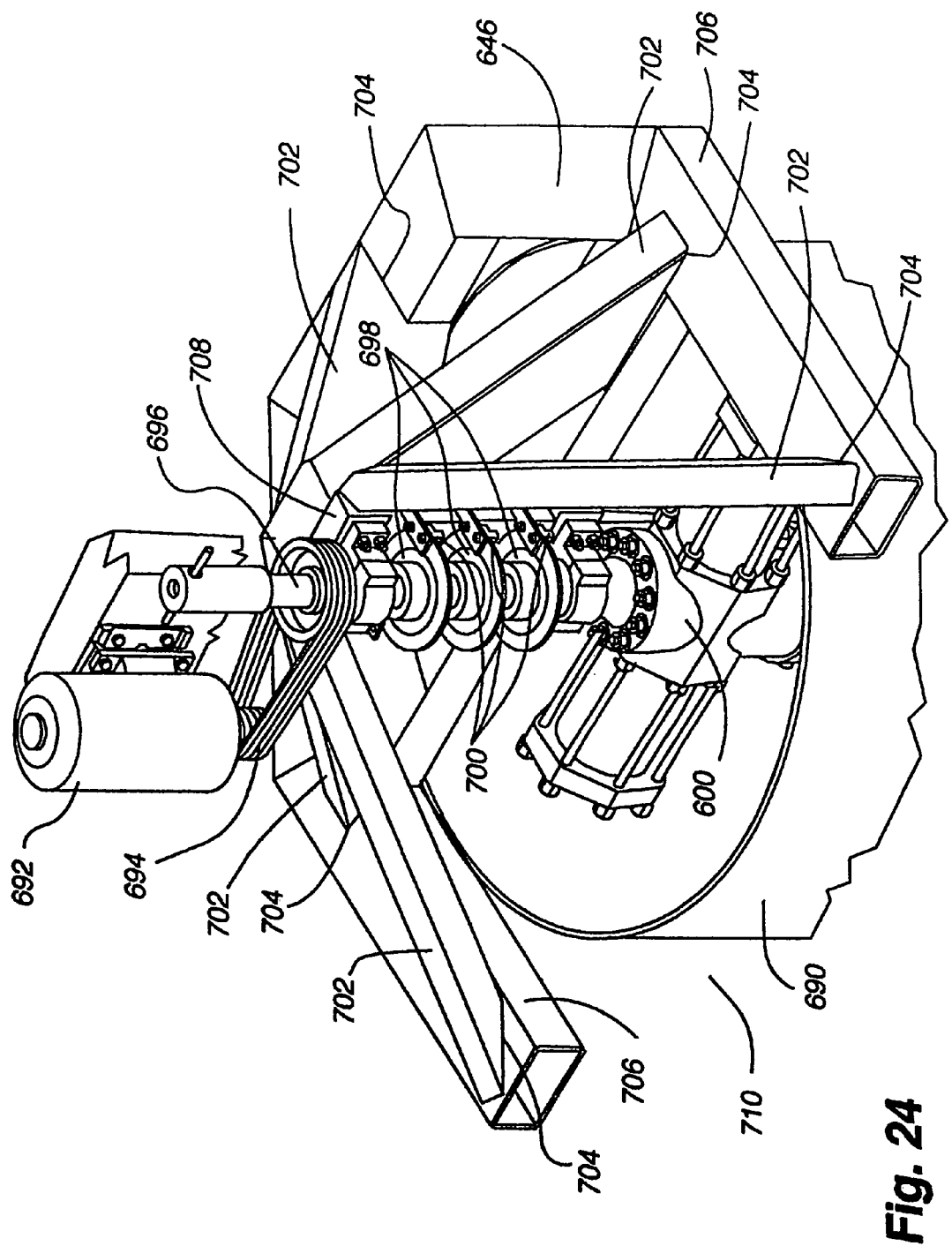
FIG. 24 is an isometric view of the frame and tank structure with the oxidation reactor suspended therefrom, including the drive motor and the breaking system.

FIGS. 22, 23 and 24 show another embodiment of the centrifuge 600 of the present invention for use as a supercritical oxidation reactor. FIG. 22 shows the centrifuge 600 of the present invention having a main body structure 602 and arm structure 604 very similar to the embodiment described with respect to FIGS. 20 and 21. In this embodiment, however, the inner tube 606 has a variety of shapes as it extends from the main body 602 of the centrifuge 600 to the distal end 608 of the arm 604. The inner tube 606 has a first length defining a cone 610 starting from a large diameter 612 attached to this main body 602 to a relatively smaller diameter 614. The inner tube 606 then transitions to a length of a cylindrical shape 616 having a constant diameter along the middle third 618 of its length. The tube 606 at the distal end 620 transitions from the cylindrical tube shape 616 to a cone 610 having a decreasing diameter to a fixed length that is cylindrical 620 and which is open. Each region is approximately one-third the length of the inner tube 606 or less.

In this embodiment, the oxidant is inserted by injectors 622 at the inner end 624 of the tubular end cap 626, near the end cap collar 628.

The auger 500, extending into each of the arms 604 inside the inner tubes 606 in the previous embodiment, is replaced by a water dispersion probe 630 having a hollow shape for carrying water. The water dispersion probe 630 extends at least partially into the inner tube 606 and extends towards the distal end 620. The probe 630 is provided with water through a piping system, one version of which is shown in FIG. 22. The probe 630 can be a continuous hollow pipe extending in either direction into each inner tube 606. The probe 630 can also be separate for each arm 604 and adjustable along the length of the inner tube 606 individually in each arm 604 by any known mechanical means for allowing such adjustment. Alternatively, the probe 630 can have a fixed length but float between the opposing arms 604 to the extent necessary based on the pressure of the oxidation reaction on the tip 631 of the probe 630. Other approximate cooling liquids could be used instead of water.

The probe 630 is a hollow tube with a curved spray end 634 having apertures 636 formed adjacent the end 634 for spraying water into the inner tube 606. The water acts as a coolant for helping control the temperature of the reaction by-products in the inner tube 606 as they flow towards the exit aperture 638, near the location of the flash point between the pressurized water and the steam. The curved end 634 of the probe 630 is an enlarged tip 631 which also acts as a choke (as described above) to help physically control the pressure as well as the resultant velocity of the reaction by-product as it passes the choke 631 towards the exit aperture 638. The water exits the probe 630 through apertures 636 formed adjacent the head 634 of the probe 630.

The centrifuge 600 in FIG. 22 is shown suspended to rotate along a vertical axis 640, causing the arms 604 to rotate through a horizontal axis 640 (see FIG. 24). The centrifuge 600 is supported by rotational bearings 642 holding onto the inlet pipe 644. The rotational bearings 642 are supported by a frame 646 which suspends the entire centrifuge 600. The arms 604 of the centrifuge 600 spin within the top portion 648 of a housing 650, thus helping keep any external object from interfering with the motion of the rotating arms 604. The exit aperture portion 638 of the housing 650 is rotatably attached to a collar 652. The collar 652 exits into a closed chamber 654. The closed chamber 654 has opposing sidewalls 656, a top wall 658 fixed to the sidewalls 656 and to the circumference or perimeter of the collar 652, and a bottom wall 662. The bottom wall 662 can consist of opposing sloped walls 664 and a horizontally positioned flat wall 666 extending between the bases 668 of the opposing sloped walls 664.

The closed chamber 654 is intended to hold a liquid, such as water, which acts as a heat sink for the reaction by-products exiting the centrifuge 600. The chamber 654 has at least one outlet 670 for the water positioned on the sidewalls 656. The chamber 654 also has at least one outlet 672 for the reaction by-products that settle to the bottom 662 of the chamber 654 for removal therefrom. The water supply line 632 for the probes 630 can pass through the sidewall 656 of the chamber 654 and attach to the bottom 674 of a water inlet feed 676 for the probe 630. The top of the water inlet feed 676 for the probe 630 is attached to the probe 630 in a fluid connection to allow the probe 630 to supply water into the inner tubes 606 as desired, for each of the instances where the probe 630 is stationary, the probe 630 is floating, or the probes 630 are independently adjustable within each arm 604.

A gas volume 678 is positioned between the top surface 680 of the water 681 and the cover 682 of the closed chamber 654. At least one gas inlet aperture 684 is formed in the sidewall 656 of the chamber 654 to allow gas to be added to or removed from that volume 678. The gas aperture 684 can be left to the atmosphere if desired. The pressure in the system can be affected by the water level on the collar 652. As the water level is raised, the back pressure on the system is increased, and as the water level is decreased in the chamber 654, the back pressure on the system is decreased. All the gas can be removed from the chamber 654 and replaced with water to maximize the back pressure adjustment. Additional water head pressure can be created by extending the chamber 654 to surround the frame 646 up along the sides 686 of the centrifuge 600 if so desired.

The collar 652 to which the centrifuge 600 is attached can be rigidly attached to the centrifuge 600 in order to spin in the water. In this instance, the cover 682 of the closed chamber 654 is sealingly yet rotatably engaged to the circumference of the collar 652. The spinning of the collar 652 can actuate the water and create a vortex which in turn can further assist in drawing the by-products from the outlet 672 and also helps mix the by-products with the water.

FIG. 23 is an enlarged view of one arm 604 of the centrifuge 600 of the embodiment shown in FIG. 22, and shows the head 634 of the probe 630 at different positions along the length of the inner tube 606.

The back pressure particular to each arm 604 and acting on the oxidation reaction zone, is affected by the position of the probe 630 along the inner tube 606. Thus the adjustment of each of the probes 630 within each of the tubes 606 respectively is an option that is helpful for fine tuning the oxidation reaction in each of the arms 604. Alternatively, with the "floating" probe 630, the probe 630 can self-adjust based on the pressure in each arm 604, with the arm 604 having the higher pressure pushing the probe 630 towards the other arm 604 to the point where the pressures are balanced at the opposing heads 634 of the floating probe 630. The oxidation reaction can be halted by moving the probe 630 away from the reaction zone and towards the main body 602 a sufficient amount to allow the pressure to drop below the critical pressure.

FIG. 24 shows the frame 646 used to suspend the centrifuge 600 in a tank 690. The motor 692 for spinning the centrifuge 600 is shown with a belt 694 attaching the motor 692 to the shaft 696 of the centrifuge 600. The braking mechanism 698 for the centrifuge is best shown in FIG. 24. It consists of a series of brake disks 698 (three are shown) attached concentrically to the input shaft 696. A brake caliper 700 is attached to the frame 646 and is positioned on each disk 698. The brake calipers 700 are used to engage the respective disks 698 either together or individually to stop the rotation of the centrifuge 600 as desired. The brake system 698 shown is one means of slowing and stopping the centrifuge 600, and can do so in approximately 30 seconds.

The frame 646 is shown having five outwardly and downwardly extending legs 702 each attached at their bottom 704 to a base frame 706, and attached at their tops 708 together to support the centrifuge 600 by its shaft 696. One side 710 of the frame 646 is open with no legs 702 to allow the centrifuge 600 to be positioned in and removed from the frame 646.

FIG. 25 is a flow chart depicting the steps involved in determining the handling of different types of input material. In particular, FIG. 24 addresses the inclusion or exclusion of the decanting step and the treatment of the input material. The process begins at Step X where the input material is analyzed to determine what type of material it is and how it should be processed, which occurs at Step Y. If the material is solids and liquids, the next operation is to ensure that the liquid exits are open in order to allow the de-watered solids to move to the reaction zone for becoming part of the oxidation reaction after which the reaction waste products exit the centrifuge. With the liquid exits open, the decanted liquid can exit the centrifuge without going through the reaction zone. If the type of material to be processed is mainly solids, the liquid exits are closed and all of the input material flows to the reaction zone to be part of the oxidation reaction. The oxidation reaction waste by-products then flow to the exit of the centrifuge.

The instant invention as used as an oxidation reactor provides several benefit as listed below.

1. Wet oxidation of subcritical and supercritical conditions is possible, based on the physical parameters required for the particular oxidation process (e.g. pressure, temperature, and oxidant content).

2. Centrifuge allows control of sludge feed density by the initial de-watering of sludge, if desired, or by the linking of two or more centrifuges together to obtain the proper moisture content in the sludge for the oxidation reaction process.

3. The user of the centrifuge combines the thickening process and the de-watering process with wet oxidation reaction.

4. This invention eliminates the need for upstream pressurization and downstream depressurization of the influent and the effluent, respectively, and the associated mechanical equipment. This is because the inlet and outlet of the centrifuge can both be at ambient pressure. It is possible that the inlet might be at an increased pressure due to the pumping of the material into the centrifuge.

5. There is greater safety affiliated with this system because of the relatively low pressure inlet fee and outlet feed.

6. The internal conditions of the reaction zone can be controlled by the speed of rotation, the inlet feed, the amount of heat energy applied, and the applied oxygen level. This control is relatively simple compared to the other supercritical oxidation reactor structures.

7. There is a relatively gradual increase of pressure on the material to be oxidized as it flows from the inlet to the reaction zone.

8. The mechanical design of the centrifuge allows replacement of maintenance wear items, i.e., the reaction chamber could be removed from the end of the arms by removing the end cap; and the inner tube, the intermediate tube and the outer tube all can be replaced individually as needed.

9. The centrifuge provides hydrostatic head on oxygen feed thereby eliminating the need for high pressure oxygen feed pump.

10. The centrifuge has a relatively low cost to operate.

11. There is a lower capital cost affiliated with this apparatus due to the large reduction in equipment, for instance, there is no requirement for specialized high pressure equipment upstream or downstream of the reaction.

12. There is likely an improved efficiency in the reaction process in this environment.

13. The centrifuge is extremely portable and easy to transport and can be taken to the site where the input material is created or more conveniently accessed.

14. The pressure gradient allows the sludge to move from subcritical to supercritical (i.e., the reaction process transitions from subcritical to supercritical oxidation reaction allowing more retention time in the reaction zone). The pressure gradient, as the sludge moves outwardly along the arm, starts at a subcritical oxidation reaction level and transitions to a supercritical oxidation reaction level.

The oxidation reactor of the present invention can treat waste having a more solid form, such as sewage sludge, where liquid can be neutralized by other means. It can also handle waste in liquid or mixed-liquid form, such as animal waste—where all material, solid and liquid needs to be processed in a centrifugal machine modified to block the liquid exit. This would allow one tube to be removed, and might require adjustment of the reaction chamber size.

The term gas as used herein is intended to include all phases of a material, including but not limited to, liquid, compressed gas, or low pressure gas. While oxygen is specifically mentioned as an oxidant, it is not exclusive, and any other gas that is useful in subcritical or supercritical oxidation reactions is sufficient.

While the invention has been particularly shown and described with reference to preferred embodiments thereof, it will be understood by those skilled in the art that various other changes in structural form and detail may be made without departing from the spirit and scope of the invention.

Presently preferred embodiments of the present invention and many of its improvements have been described with a degree of particularity. It should be understood that this description has been made by way of example, and that the invention is defined by the scope of the following claims.

What is claimed is:

1. A method of using a centrifuge to separate a light material that is within an input mixture from a heavy material that is within the input mixture, while at the same time independently controlling a speed of rotation of the centrifuge and a speed of removal of the heavy material from the centrifuge, comprising the steps of:

providing a first and a second arm assembly aligned on an arm-axis and that are rotatable in a plane extending generally perpendicular to a rotation-axis;

providing that each of said first and second arm assemblies includes a tubular-housing having a closed outer end, an intermediate tube having an open outer end, and an inner tube having an open outer end;

providing that said inner tube of each arm assembly is of a given length;

providing that said intermediate tube of each arm assembly is of a length that is less than said given length;

providing that an outer end of said tubular-housing of each arm assembly is spaced from said outer end of said intermediate tube and from said outer end of said inner tube;

providing an input mixture flow path that communicates with a cylindrical space between said intermediate tube and said inner tube of each arm assembly;

providing a heavy material flow path that communicates with a space within said inner tube of each arm assembly;

providing a light material flow path that communicates with a cylindrical space between said intermediate tube and said tubular-housing of each arm assembly;

providing a conveyer screw within the inner tube of each arm assembly;

providing first speed controllable drive means connected to effect rotation of said first and second arm assemblies about said rotation-axis; and providing second speed controllable drive means connected to effect rotation of said conveyer screws.

2. The method of claim 1 wherein said first speed-controllable drive means is an electric motor and wherein said second speed-controllable drive means is a hydraulic motor.

3. The method of claim 2 wherein said rotation-axis extends in a horizontal direction.

4. In a centrifuge wherein a light material within an input mixture is separated from a heavy material within the input mixture, the centrifuge including a first and a second axially aligned arm assembly rotatable in a plane that extends generally perpendicular to an axis of rotation, wherein each of the first and second arm assemblies includes a tubular-housing having a closed outer end, an intermediate tube having an open outer end, and an inner tube having an open outer end, wherein the inner tube of each arm assembly is of a given length, wherein the intermediate tube of each arm assembly is of a length that is less than the inner tube, wherein the outer end of the tubular-housing of each arm assembly is spaced from the outer end of the intermediate tube and from the outer end of the inner tube, wherein an input mixture input-flow-path communicates with a space between the intermediate tube and the inner tube of each arm assembly, wherein a heavy material output-flow-path communicates with a space within the inner tube of each arm assembly, and wherein a light material output-flow-path communicates with a space between the intermediate tube and the tubular-housing of each arm assembly, a method of mounting the inner ends of the tubular-housing, the intermediate tube and the inner tube of each arm assembly to a central member that rotates about the axis of rotation, comprising the steps of:

securing the inner end of the tubular-housing of each arm assembly to opposite sides of the central member, providing a first mounting ring on the inner end of the tubular housing of each arm assembly, the first mounting ring having an inward-facing portion;

providing a second mounting ring on an inner end of the intermediate tube of each arm assembly, the second mounting ring having an inward-facing portion, and the second mounting ring having an outward facing portion secured to the inward-facing portion of the first mounting ring; and providing a third mounting ring on an inner end of the inner tube of each arm assembly, the third mounting ring having an inward-facing portion secured to the outward-facing portion of the second mounting ring.

5. The method of claim 4 wherein and the outward facing portion of the second mounting ring physically underlies the inward-facing portion of the first mounting ring, and wherein the outward-facing portion of the second mounting ring overlies the inward-facing portion of the third mounting ring.

6. The method of claim 5 wherein the axis of rotation is a horizontal axis.

\* \* \* \* \*